(12) United States Patent
Tass et al.

(10) Patent No.: US 8,721,695 B2
(45) Date of Patent: May 13, 2014

(54) DEVICE AND METHOD FOR STIMULATING NEURONAL TISSUE BY MEANS OF OPTICAL STIMULI

(75) Inventors: Peter A. Tass, Munich (DE); Marcus Goetz, Heidelberg (DE); Bernhard Pelz, Heidelberg (DE); Stefan Fischer, Heidelberg (DE); Jean-Christophe Roulet, Ligniéres/Ne (CH); Urban Schnell, Muenchenbuchsee/Be (CH)

(73) Assignees: Forschungszentrum Juelich GmbH, Juelich (DE); ANM Adaptive Neuromodulation GmbH, Cologne (DE)

( * ) Notice: Subject to any disclaimer, the term of this patent is extended or adjusted under 35 U.S.C. 154(b) by 348 days.

(21) Appl. No.: 12/815,691

(22) Filed: Jun. 15, 2010

(65) Prior Publication Data

US 2010/0324631 A1      Dec. 23, 2010

(30) Foreign Application Priority Data

Jun. 18, 2009   (DE) .......................... 10 2009 025 407

(51) Int. Cl.
*A61N 5/06*       (2006.01)
*A61B 19/00*    (2006.01)

(52) U.S. Cl.
USPC ................. 607/88; 607/89; 128/898

(58) Field of Classification Search
USPC ....................... 607/88–94; 128/898
See application file for complete search history.

(56) References Cited

U.S. PATENT DOCUMENTS

| | | | |
|---|---|---|---|
| 6,921,413 B2 | 7/2005 | Mahadevan-Jansen et al. | |
| 7,288,108 B2 | 10/2007 | DiMauro et al. | |
| 2004/0002635 A1* | 1/2004 | Hargrove et al. ............. | 600/300 |
| 2005/0149123 A1* | 7/2005 | Lesser et al. ...................... | 607/2 |
| 2005/0216072 A1 | 9/2005 | Mahadevan-Jansen et al. | |
| 2006/0155348 A1 | 7/2006 | deCharms | |
| 2006/0212089 A1 | 9/2006 | Tass | |
| 2007/0025608 A1* | 2/2007 | Armstrong ................... | 382/132 |

FOREIGN PATENT DOCUMENTS

EP    1 613 394 A1    1/2006

* cited by examiner

*Primary Examiner* — Dawayne A Pinkney
(74) *Attorney, Agent, or Firm* — Dickstein Shapiro LLP

(57) ABSTRACT

A device with a control unit and a plurality of stimulation units configured to be implanted in the body of a patient and generate optical stimuli, wherein the optical stimuli reset the phase of the neuronal activity of the neurons during the stimulation of neurons exhibiting abnormally synchronous and oscillatory neuronal activity, and the control unit is configured to actuate the stimulation units such that at least two of the stimulation units reset the phases of the respectively stimulated neurons at different times.

11 Claims, 20 Drawing Sheets

DEVICE AND METHOD FOR STIMULATING NEURONAL TISSUE BY MEANS OF OPTICAL STIMULI

CROSS-REFERENCE TO RELATED APPLICATION

This application claims priority to German Patent Application Serial No. 10 2009 025 407, which was filed on Jun. 18, 2009, and is incorporated by reference in its entirety.

TECHNICAL FIELD

The application relates to a device and a method for stimulating neuronal tissue by means of optical stimuli.

BACKGROUND

Several neurological and psychiatric diseases have excessively strong neuronal activity synchronization processes in the brain. Here, nerve cell networks exhibit abnormal, e.g. excessively synchronous, activity in circumscribed regions of the brain, e.g. the thalamus and the basal ganglia. In this case, a large number of neurons synchronously form action potentials, i.e. the involved neurons fire excessively synchronously, as a result of which the function of the brain is massively impaired. By contrast, in healthy individuals the neurons fire in a qualitatively different fashion in these regions of the brain, e.g. in an uncorrelated fashion.

If medicament-based therapy fails, neurological and psychiatric diseases with excessively strongly pronounced neuronal synchronization are to date treated by electric brain stimulation.

BRIEF DESCRIPTION OF THE FIGURES

In the following text, the exemplary embodiments are explained in more detail with reference to the drawings, in which.

DETAILED DESCRIPTION

Figure 1:
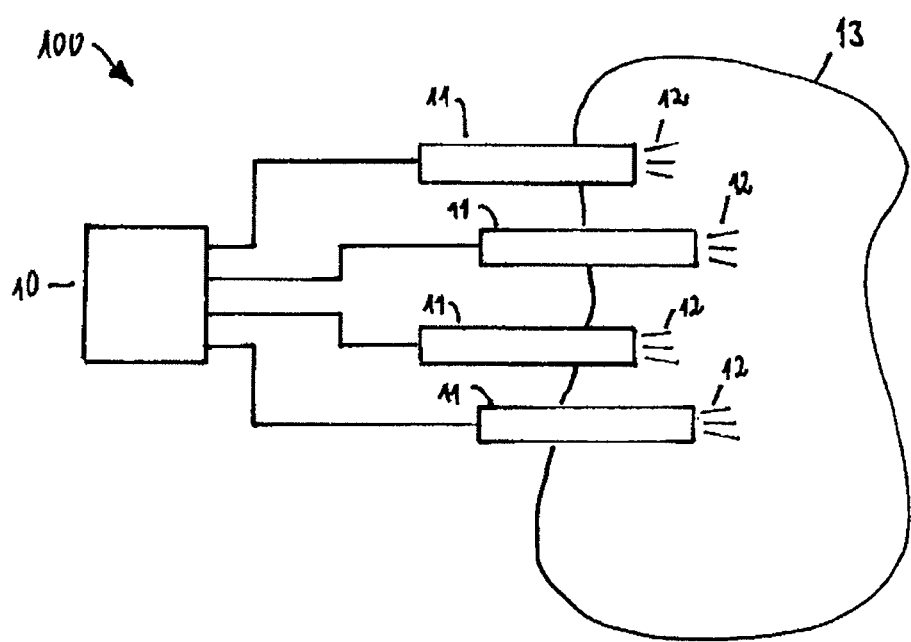
FIG. 1 shows a schematic illustration of a device for optical stimulation as per an exemplary embodiment during operation.

FIG. 1 schematically illustrates a device 100 for optical stimulation of neuronal tissue. The device 100 consists of a control unit 10 and a plurality of stimulation units 11. During the intended operation of the device 100, at least the stimulation units 11 are implanted into the body of a patient and there said units generate optical stimuli 12 by means of which neuronal tissue 13 of the patient is stimulated.

The following text explains the functioning of the device 100. The function of the device 100 is also described on the basis of method steps. The device 100 is provided with means that can carry out all steps of the described treatment methods. Therefore, the disclosed method steps should implicitly also disclose means for carrying out the method steps. Thus, the method steps also simultaneously constitute the functionalized device features.

Figure 2A:
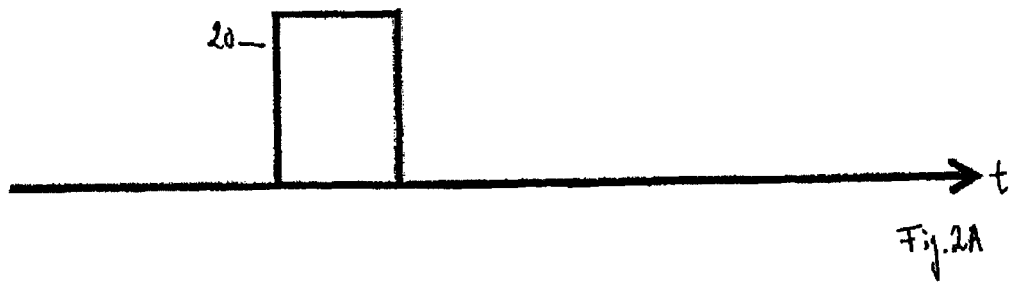
FIGS. 2A to 2W show schematic illustrations of differently formed individual stimuli for optical stimulation.
Figure 2B:
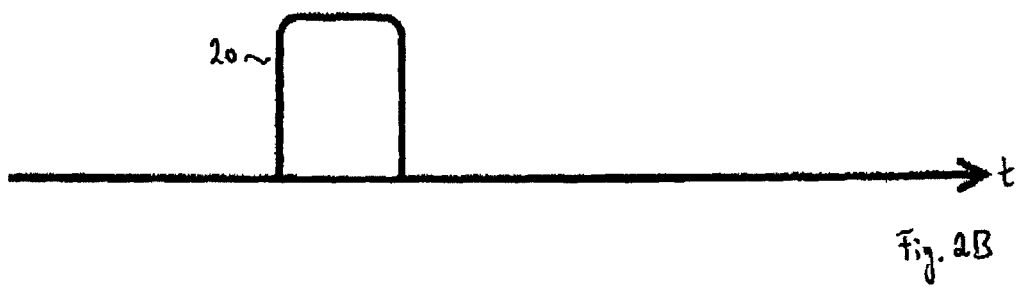
Figure 2C:
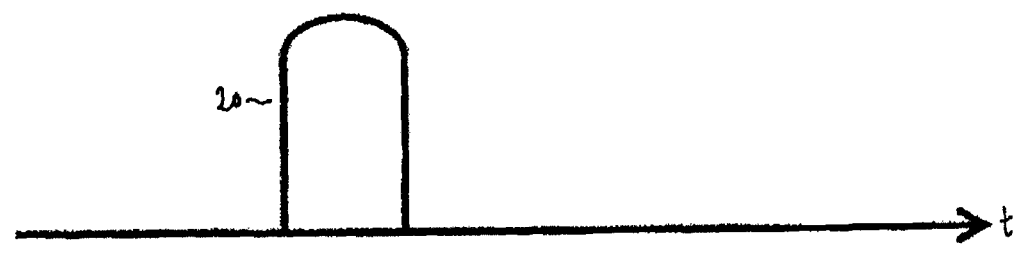
Figure 2D:
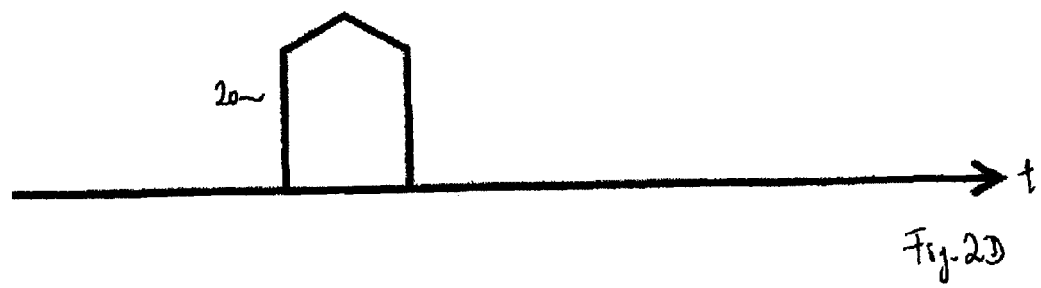
Figure 2E:
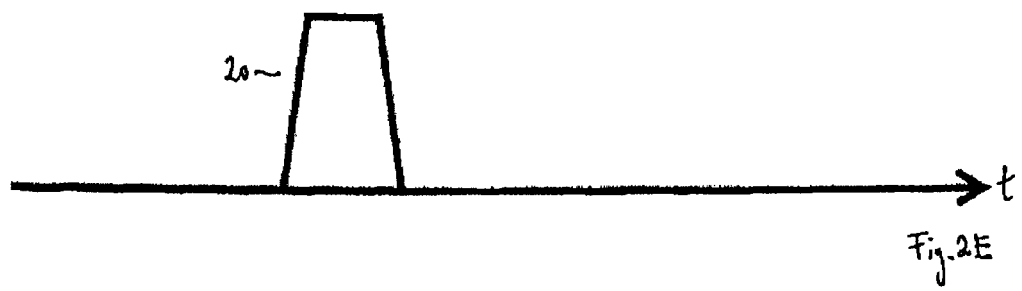
Figure 2F:
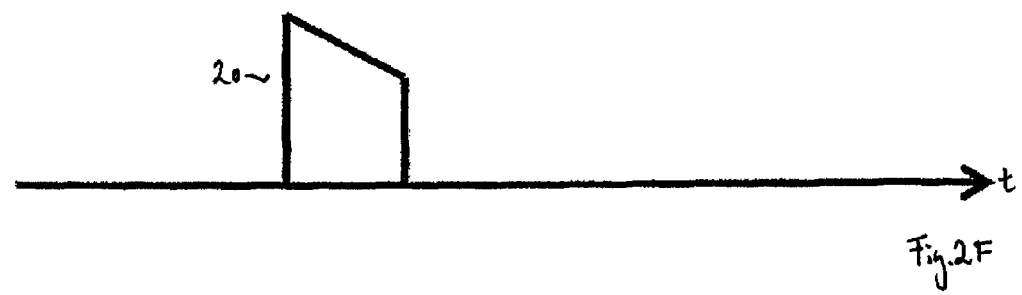
Figure 2G:
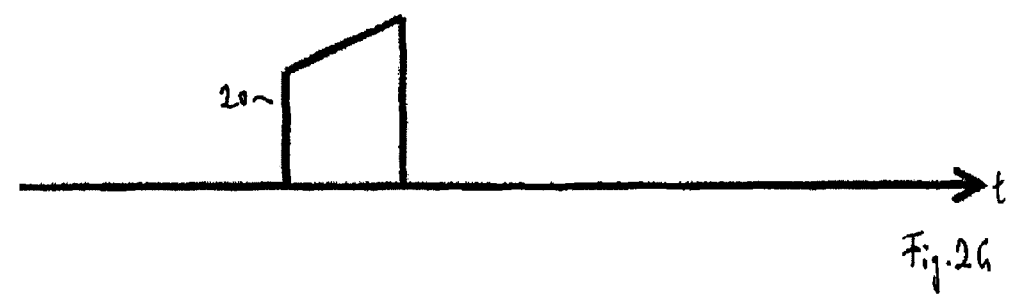
Figure 2H:
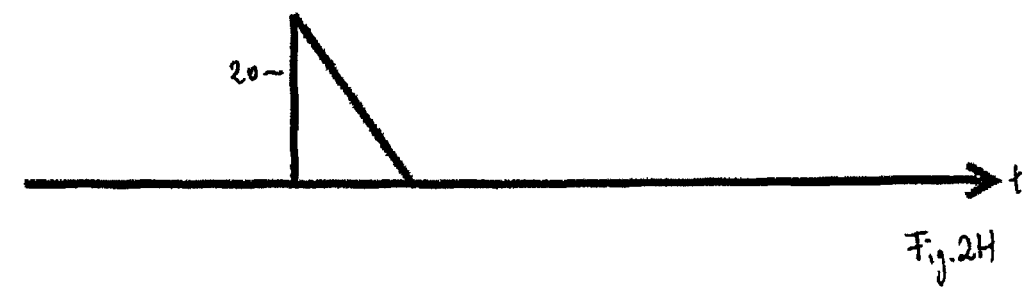
Figure 2I:
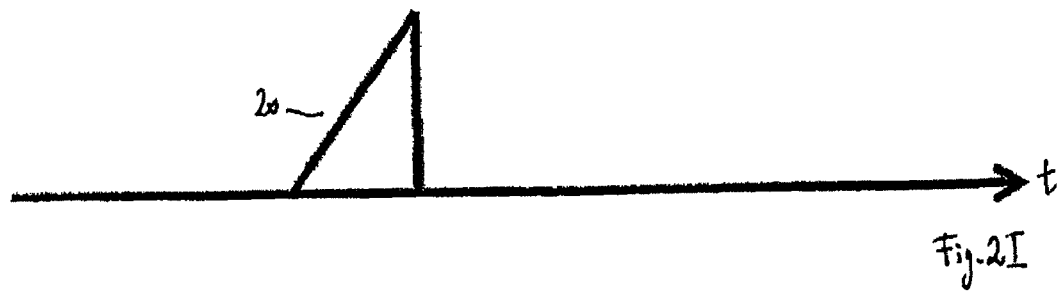
Figure 2J:
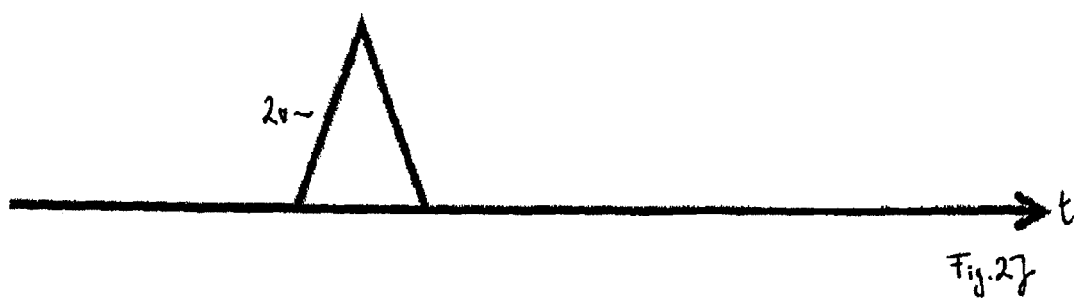
Figure 2K:
Figure 2L:
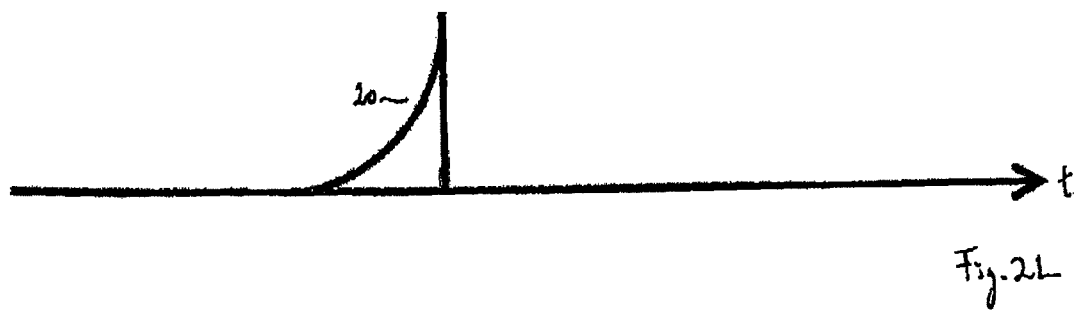
Figure 2M:
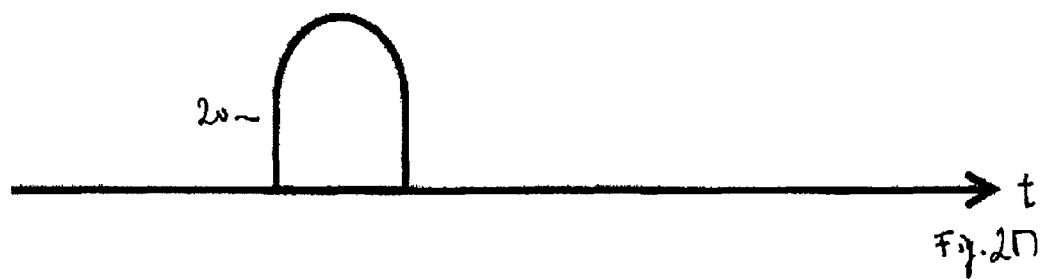
Figure 2N:
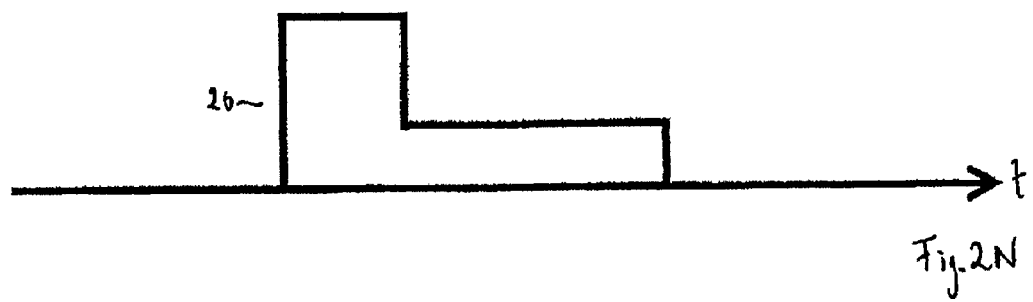
Figure 2O:
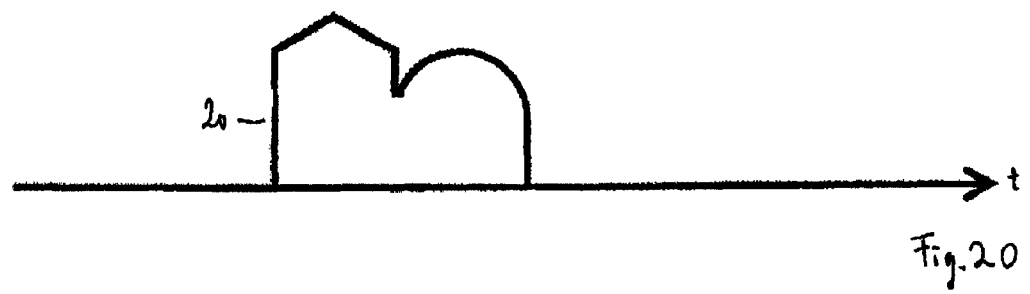
Figure 2P:
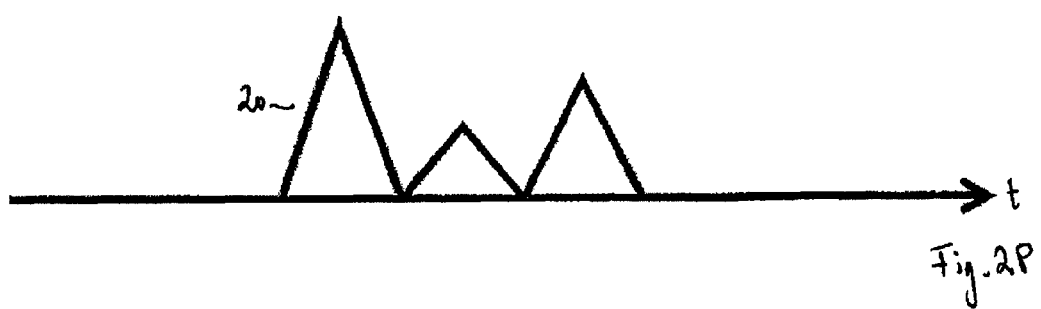
Figure 2Q:
Figure 2R:
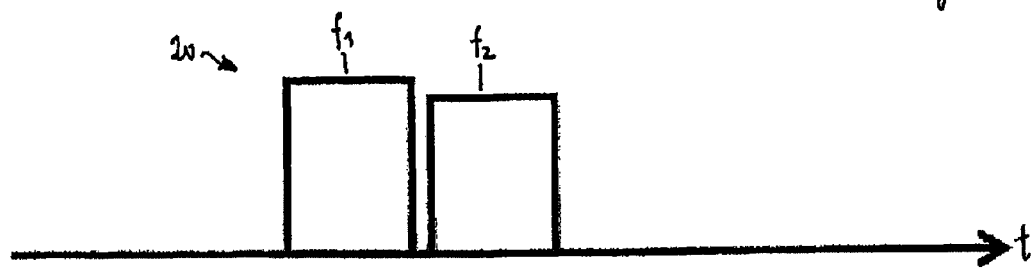
Figure 2S:
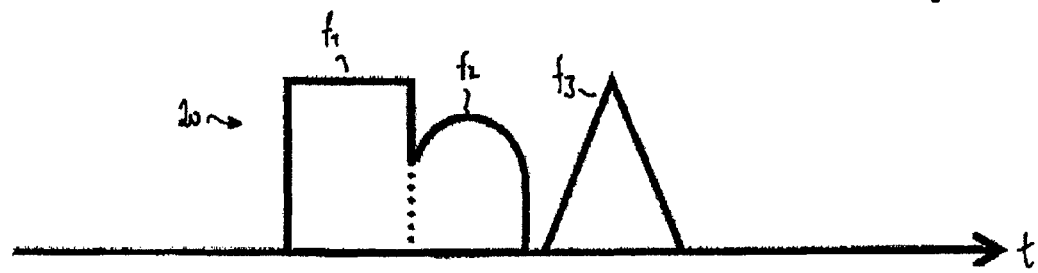
Figure 2T:
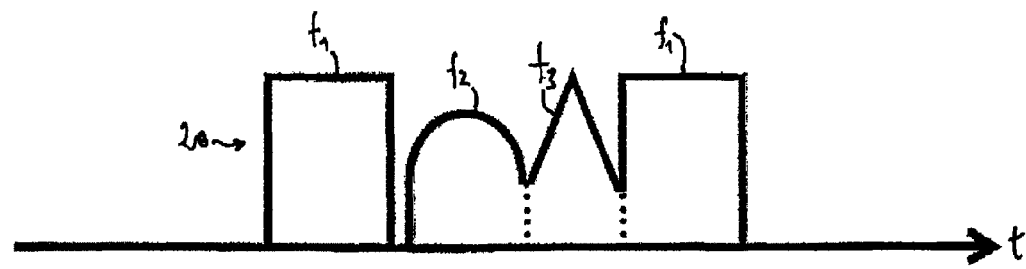
Figure 2U:
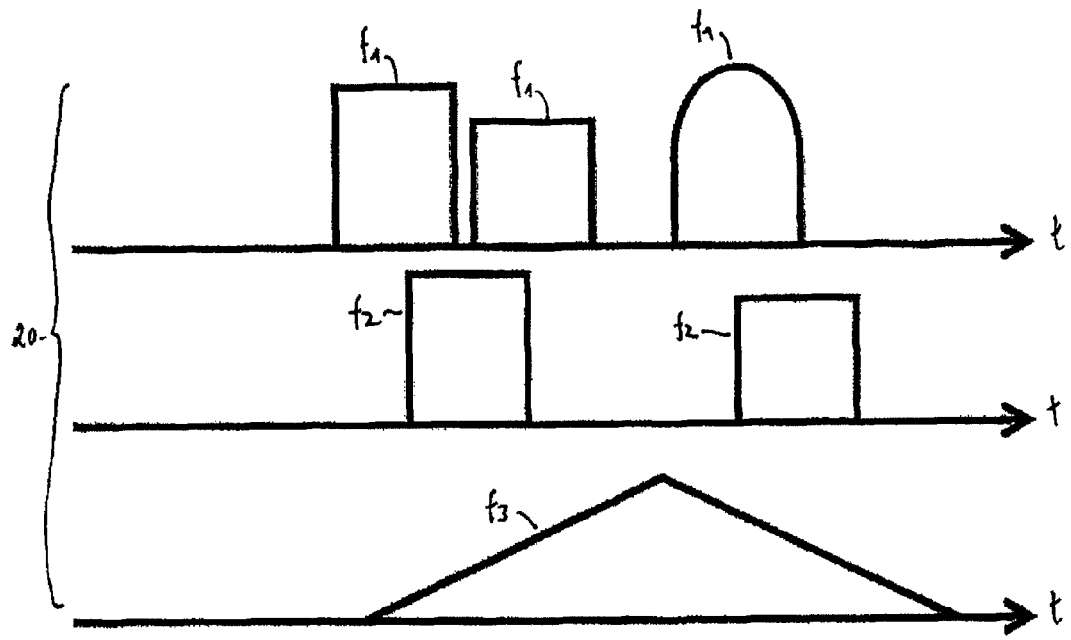
Figure 2V:
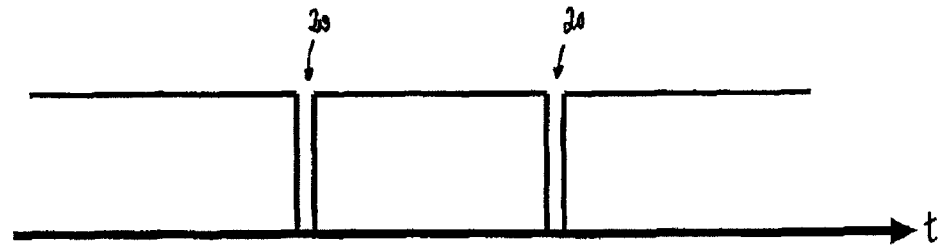
Figure 2W:
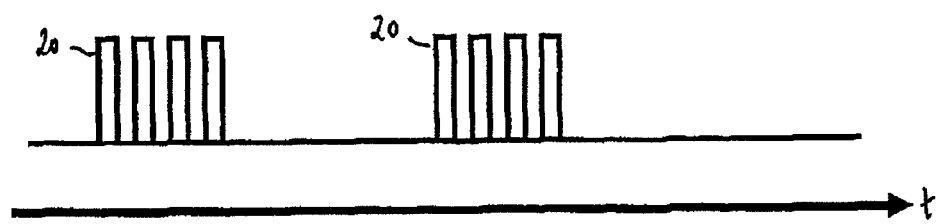

The optical stimuli 12 applied by the respective stimulation units 11 can be individual stimuli 20, as shown in an exemplary fashion in FIGS. 2A to 2W, or can be made up of such individual stimuli 20. In FIGS. 2A to 2W, the intensity (y-axis) of the individual stimuli 20 is plotted in each case over time t (x-axis). The duration of an individual stimulus 20 can lie in the region of 1 ps to 200 μs, or more. The electromagnetic radiation making up the optical stimuli 12 can be visible light with wavelengths between 380 and 780 nm, or infrared radiation with wavelengths between 780 and 3000 nm (or up to 10 000 nm or more). It is also feasible for electromagnetic radiation with other wavelengths to be used as the optical stimuli 12.

The individual stimuli 20 can have different shapes. For elementary individual stimuli 20, use can be made of, for example, rectangular pulses (cf. FIG. 2A) and corresponding derivatives (cf. FIGS. 2B to 2G). Here, the corners of the rectangular pulse 20 (cf. FIG. 2B) or the central part (cf. FIG. 2C) can be chamfered or rounded, or else the central part can have a symmetric roof-like design (cf. FIG. 2D). Furthermore, the rising and/or falling edges of the rectangular pulse can be beveled (cf. FIG. 2E), or else the rising or falling edge can be made higher than the respective other edge of the pulse 20 (cf. FIG. 2F or 2G).

Moreover, the individual stimuli 20 can be formed as, for example, triangular pulses. Here, either the rising or falling edge can be made to be steep (cf. FIG. 2H or 2I), or the triangular pulse can be symmetric (cf. FIG. 2J). Moreover, the pulse 20 can have a steep rising edge and a curved, e.g. exponentially decreasing, falling edge (cf. FIG. 2K), wherein the two edges can also be interchanged (cf. FIG. 2L). The central part of the pulse can likewise be curved (cf. FIG. 2M) as well.

However, the individual stimuli 20 do not have to have the above-described simple geometric shapes. Rather, the individual stimuli 20 can also be composed of different individual pulses made of elementary geometric shapes and the same light wavelength. By way of example, an individual stimulus 20 can be composed of a shorter, stronger and a weaker, longer pulse (cf. FIG. 2N). Furthermore, by way of example, an individual stimulus 20 can be composed of individual pulses, as shown in e.g. FIGS. 2D and 2M, in immediate succession (cf. FIG. 2O). Or else, an individual stimulus 20 can be constructed from three successive individual stimuli of differing intensity (FIG. 2P). Individual stimuli 20 can also be continuous waveforms with the same light frequency (cf. FIG. 2Q).

The individual stimuli 20 can also consist of individual pulses of differing light frequency (cf. FIGS. 2R to 2U). The individual pulses of differing light frequency can, for example, be applied successively in time. Thus, an individual stimulus 20 can consist of, for example, two rectangular pulses with differing light frequencies $f_1$ and $f_2$ and differing intensity (cf. FIG. 2R). Furthermore, the shapes of the pulse components of differing frequency $f_1$, $f_2$ and $f_3$ can differ (cf. FIGS. 2S and 2T), wherein the dashed lines in FIGS. 2S and 2T indicate at what point in time the light frequency is switched.

The individual pulses with differing frequency do not necessarily have to be applied in succession; rather, they can be applied at the same time or overlapping in time (cf. FIG. 2U). The overall stimulus in the example shown in FIG. 2U results from the sum of the individual pulses at the respective time, i.e. the mixture is summed vertically at all times.

Moreover, the individual stimuli 20 can also be negative impulses, in which the tissue is irradiated by an optical DC power and stimulated by negative impulses with a given frequency and shape (cf. FIG. 2V).

The individual stimuli 20 can also be applied with an optical offset; this means that the tissue is irradiated by a constant optical DC power, which is superposed by positive impulses with a given frequency and shape (cf. FIG. 2W).

Different frequencies of the light used for stimulation can trigger different effects in the nerve tissue, as a result of which the control effect of the light stimulation can be further improved. Also, the different penetration depths of the light at different frequencies can relatively selectively actuate nerve tissue at different depths (i.e. at a different distance from the respective stimulation location). By way of example, laser light at an expedient frequency can attain a particularly large penetration depth. Laser light at a less expedient frequency with a comparable intensity cannot attain such a large penetration depth, and so e.g. only part of the neuronal population or part of the fiber bundle in the vicinity of the stimulation location can be stimulated. Furthermore, higher light intensity generally can also attain a larger penetration depth into the tissue. That is to say the frequency and intensity parameters allow different stimulation effects to be obtained.

Figure 3:
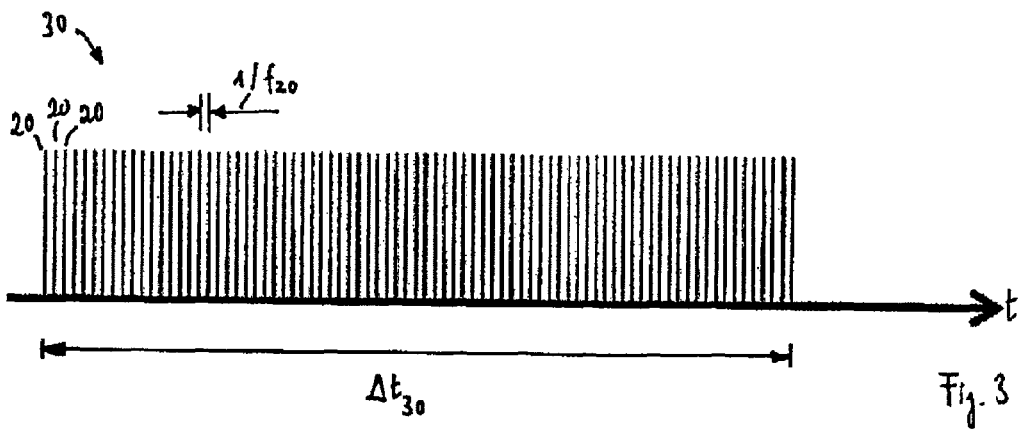
FIG. 3 shows a schematic illustration of a periodic pulse train of finite length for optical stimulation.

The individual stimuli 20, mentioned above in an exemplary fashion, can be dispensed either as individual stimuli 20 or as succession 30 (or group) of individual stimuli 20, for example as a periodic pulse train 30 of finite length as illustrated in FIG. 3, wherein the pulse train 30 is dispensed by one or more stimulation units 11. Examples of such a periodic pulse train 30 include:

(i) Duration of the individual stimuli 20 between one and a few picoseconds (e.g. up to 10 ps). Frequency $f_{20}$ of the periodic pulse train 30, i.e. repetition rate of the individual stimuli 20 within the pulse train 30, between 1 and a plurality of gigahertz (e.g. up to 100 GHz). Duration $\Delta t_{30}$ of the individual periodic pulse train 30 in the region of 1 to a plurality of microseconds (e.g. up to 100 µs).

(ii) Duration of the individual stimuli 20 between 1 and 200 microseconds. Frequency of the periodic pulse train 30 between 100 and 200 Hertz. Length of the periodic pulse train between 2 and 20 individual stimuli.

Instead of the periodic pulse train 30 shown in FIG. 3, it is also possible to use variants thereof:

(i) Use can be made of other individual stimuli 20, e.g. the individual stimuli 20 shown in FIGS. 2A to 2W.

(ii) The frequency $f_{20}$ within the periodic pulse train 30 can be varied. For example, the frequency $f_{20}$ can rise or fall within the periodic pulse train 30.

(iii) Instead of a (strictly) periodic pulse train 30, the succession of the pauses between the individual stimuli 20 within the pulse train 30 can also be varied stochastically and/or deterministically (e.g. chaotically).

In the following text, a succession 30 of individual stimuli 20, as described above and illustrated in an exemplary fashion in FIG. 3, is referred to as a macro-stimulus 30. In respect of the temporal structure of the stimulus application, the macro-stimuli 30 can be applied periodically or otherwise deterministically (e.g. chaotically) or stochastically or mixed deterministically-stochastically by means of the various stimulation units 11.

The device 100 can in particular be used for the treatment of neurological or psychiatric diseases, e.g. Parkinson's disease, essential tremor, dystonia, spasticity, epilepsy, tremor in a condition after concussion, Alzheimer's disease, spinocerebellar ataxia, pain therapy, depression, motor disturbance, cerebellar disease, obsessive disorders, Tourette's syndrome, functional disorder after a stroke, spasticity, tinnitus, sleep disorders, schizophrenia, substance dependences, personality disorders, attention-deficit disorder, attention-deficit hyperactivity disorder, pathological gambling, neuroses, borderline personality disorder, bulimia, burnout syndrome, fibromyalgia, migraine, cluster headache, general headache, neuralgia, ataxia, tic disorder or hypertonia, but also other diseases.

The aforementioned diseases can be caused by a disorder in the bioelectric communication of neural networks connected in specific circuits. Herein, a neuron population continuously generates abnormal neuronal activity and possibly an abnormal connectivity (network structure) associated therewith. In the process, a large number of neurons form action potentials at the same time, i.e. the involved neurons fire in an overly synchronous fashion. Additionally, the sick neuron population exhibits an oscillatory neuronal activity, i.e. the neurons fire rhythmically. In the case of neurological or psychiatric diseases, the average frequency of the abnormal rhythmic activity of the affected neural networks lies approximately between 1 and 30 Hz, but it can also lie outside of this range. By contrast, the neurons fire qualitatively differently in healthy humans, e.g. in an uncorrelated fashion.

In the case of Parkinson's disease, there is overly synchronous, rhythmic neuronal activity in the region of the basal ganglia (e.g. STN=subthalamic nucleus) and the thalamus (e.g. VIM=ventrointermediate nucleus of the thalamus), i.e.

peaks in the frequency spectrum of the local field potential (LFP), in the vicinity of approximately 5 Hz (in the tremor frequency range) and in the alpha range (7 to 12 Hz) and beta range (13 to 30 Hz).

In order to desynchronize an abnormal rhythm in a targeted fashion, the frequency $f_{30}$, at which the macro-stimuli 30 are dispensed via individual stimulation units 11, can be matched to the frequency of the abnormal rhythm, i.e. the frequency $f_{30}$ corresponds to the pathological peak frequency in the LFP±25%. By way of example, the frequency $f_{30}$ can lie in the range between 1 and 30 Hz and, more particularly, in the range between 1 and 20 Hz or in the range between 5 and 20 Hz or in the range between 10 and 30 Hz, but can also assume smaller or greater values.

However, the stimulation can also be brought about without precise matching because the stimulation effect is robust in respect of trimming of this parameter. The stimulation period $T=1/f_{30}$ virtually forms the periodic frame for the application of the macro-stimuli 30 (cf. FIGS. 4 to 6).

Figure 4:
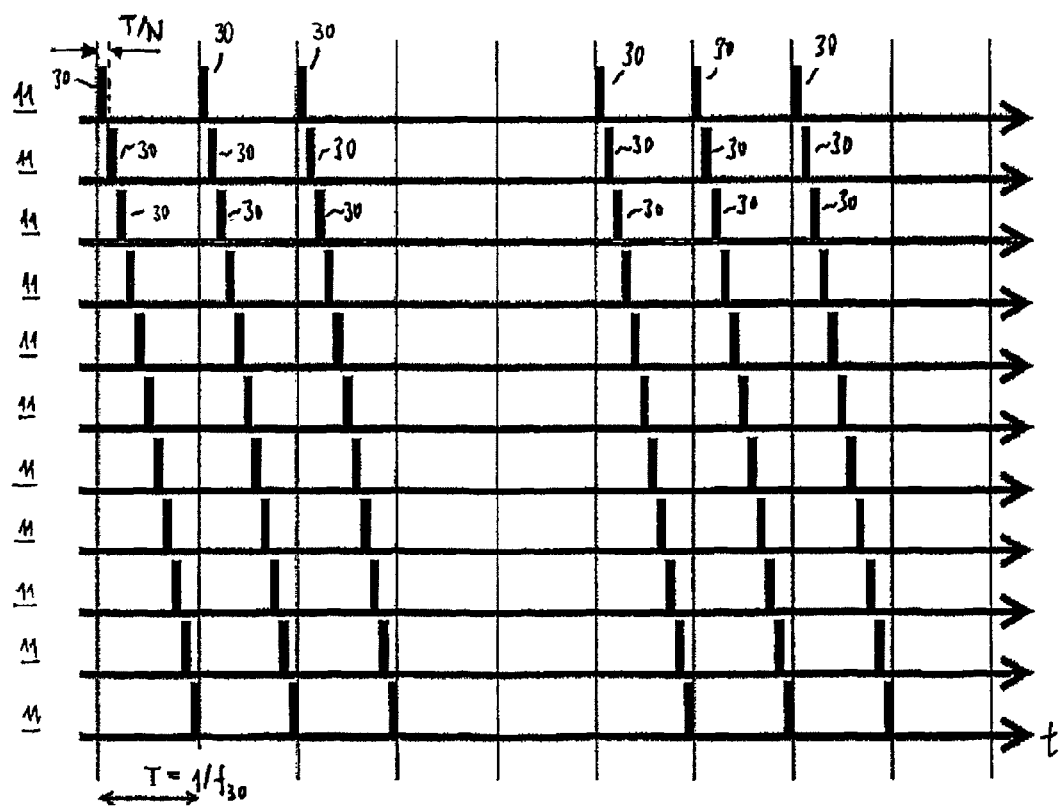
FIG. 4 shows a schematic illustration of an application of optical macro-stimuli by means of a plurality of stimulation units.

A stimulation method suitable for the above-described purposes, which method can, for example, be carried out by the device 100, is illustrated schematically in FIG. 4. Plotted therein over time t, one below the other, are the optical stimuli 12 applied by the individual stimulation units 11. In the example shown in FIG. 4, the optical stimuli are dispensed with the aid of eleven stimulation units 11. The illustrated black bars in each case represent one macro-stimulus 30.

By way of example, optical stimuli are applied in k successive stimulation periods T and then no stimuli are applied in m successive stimulation periods T (k, m are natural numbers). This temporal pattern can be repeated periodically: k cycles (=stimulation periods T) ON (=with stimulation), m cycles OFF (=without stimulation), k cycles ON, m cycles OFF, etc. In the examples shown in FIGS. 4 and 5, the stimulation pattern is 3 cycles ON, 2 cycles OFF. In FIG. 6, the stimulation pattern is 4 cycles ON, 3 cycles OFF. In another embodiment, the parameters k and m can also be varied over time, e.g. periodically, chaotically or otherwise deterministically, or else stochastically or mixed deterministically/stochastically.

Provision can be made for optical stimuli 12 to be applied by all available stimulation units 11 of the device 100 or by a subset thereof. The subset of the stimulation units 11 used for the stimulation can be selected on the basis of advance information, e.g. anatomical information obtained by means of imaging methods and/or functional information obtained by means of (separate) micro-deductions (carried out with a different instrument). The subset of the stimulation units 11 used for the stimulus can however also be determined by functional tests (test stimulations via a subset of stimulation locations changing within the scope of the selection method) and/or measurements of electrophysiological parameters via measurement contacts housed in a structurally unified fashion.

The overall number of the stimulation units 11 (=stimulation locations) finally used for the optical stimulation should be referred to by N. The stimulation period T is divided by the number N of the stimulation units 11 and so the stimulation period T is subdivided into equal parts T/N. By way of example, a macro-stimulus 30 can be applied at a respectively different stimulation location at the beginning of each such part, as illustrated in FIG. 6. However, there can also be deviations from this temporal scheme by up to ±10% or ±25% and more. This does not cause the stimulation to lose its effectiveness.

According to the embodiment shown in FIG. 4, the macro-stimuli 30 are always applied sequentially in the same order via the N stimulation units 11 during each stimulation period T.

Figure 5:
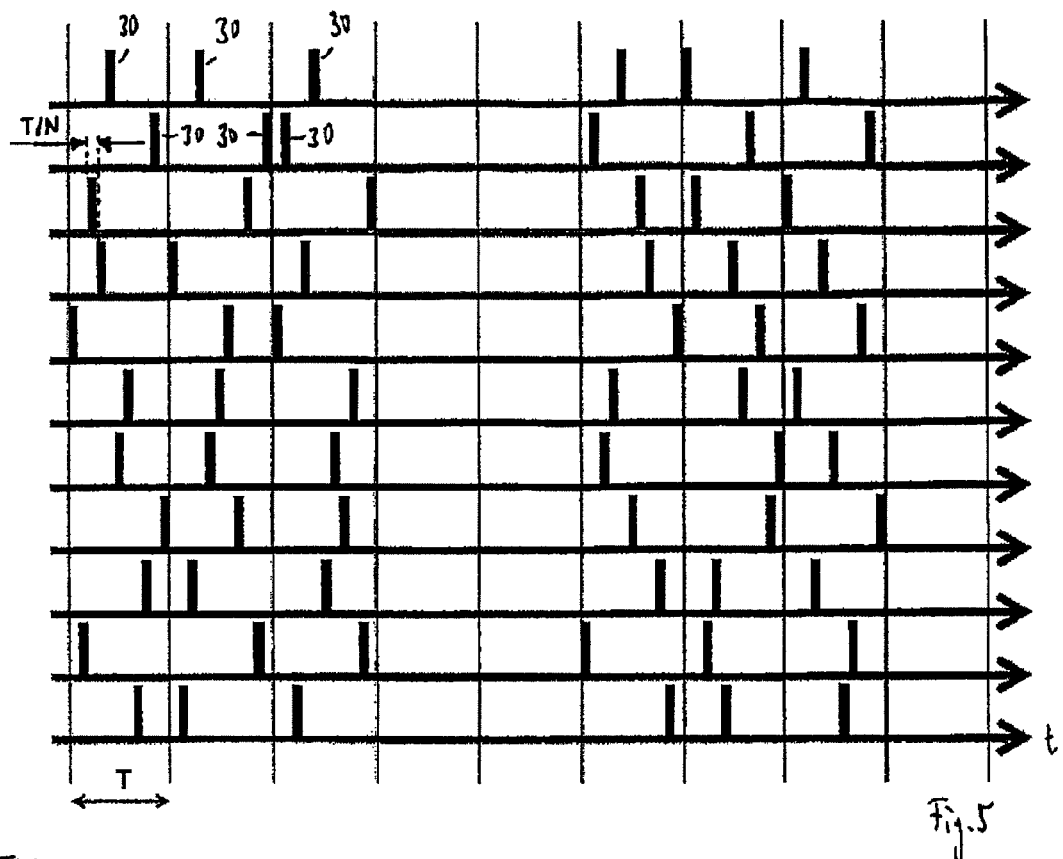
FIG. 5 shows a schematic illustration of a variation of the stimulus application shown in FIG. 4.
Figure 6:
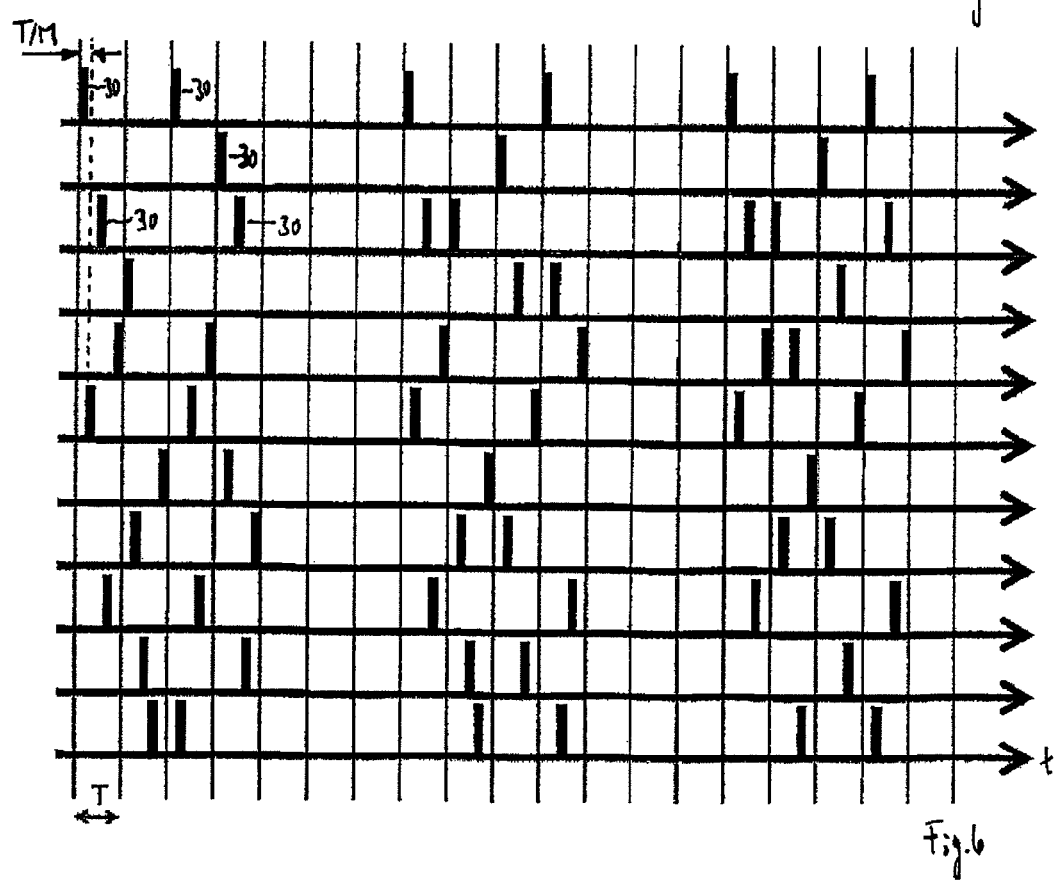
FIG. 6 shows a schematic illustration of a further variation of the stimulus application shown in FIG. 4.

As shown in FIG. 5, the sequence of the macro-stimuli 30 can also be varied stochastically during each stimulation period.

The selection of the sequence of the stimulation units 11 within a stimulation period T can also be brought about with more complex e.g. deterministic (e.g. chaotic) and mixed deterministic/stochastic algorithms.

According to a further embodiment, illustrated in FIG. 6 in an exemplary fashion, N stimulation units 11 are selected for optical stimulation. Of these N stimulation units 11 selected for stimulation, only a subset of M stimulation units 11 (M<N) is stimulated during each stimulation period T. For this, the stimulation period T is divided by the number of activated optical waveguides M and so the stimulation period T is subdivided into equal parts T/M. Since the stimulation effect is robust, there can be deviations of up to ±10% or ±25% and more from this temporal pattern.

The selection of the M stimulation locations activated in the respective stimulation period T and, more particularly, the order thereof can be brought about stochastically or deterministically or mixed stochastically/deterministically. By way of example, in FIG. 6, macro-stimuli 30 are applied to 5 (from a total of 11) stimulation locations during each stimulation period T, i.e. M=5, N=11. The selection of these 5 stimulation locations and their order within a stimulation period T is brought about periodically.

Moreover, the stimulation can be brought about by a subset of the selected stimulation units 11 that varies over time. For this, N stimulation units 11 are first of all selected for optical stimulation as described above. Of these N stimulation units 11 selected for stimulation, only a subset of, on average over time, M (M<N) stimulation units 11 is stimulated during each stimulation period T. For this, the stimulation period T is divided by the number M of the activated stimulation units 11: the stimulation period T is subdivided into equal parts T/M. In the respective stimulation period T, there can be stimulation at precisely M or at more than M or at less than M stimulation locations.

In the case of stimulation over a subset of the selected stimulation units 11 that can vary over time, at least two stimulation locations can be activated simultaneously at a particular time if more than M stimulation locations are activated during a stimulation period T. However, at least one surplus stimulation location outside of the order of the temporal activation scheme can also be activated. If less than M stimulation locations are activated during a stimulation period T, the activation of at least one stimulation location is skipped. The selection of the stimulation locations activated during the respective stimulation period T is brought about by deterministic or stochastic or mixed deterministic-stochastic algorithms.

Moreover, the temporal succession can be matched to the variable subset of the selected stimulation locations. The number of the stimulation units 11 activated during the j-th stimulation period should be referred to as $M_j$. The selection of the numbers $M_1$, $M_2$, $M_3$ etc. is brought about by a deterministic or stochastic or mixed deterministic-stochastic algorithm. Within the j-th stimulation period, the $M_j$ stimulation units 11 are activated spaced apart by time intervals of equal length, i.e. they are respectively activated successively with a pause of $T/M_j$. However, it is also possible to deviate from this temporal pattern by up to ±10% or ±25%.

Instead of the above-described periodic application of macro-stimuli 30, the latter can also be applied in a non-periodic fashion. In the following observations, the assumption is made that a total of N stimulation locations are selected for the optical stimulation. A macro-stimulus 30 is applied at the j-th stimulation location at the times $\tau_1^{(j)}$, $\tau_2^{(j)}$, $\tau_3^{(j)}$, $\tau_4^{(j)}$, . . . . Here, the same macro-stimulus 30 can be applied each time. However, the parameters of the utilized macro-stimuli 30 can also be varied according to a deterministic or stochastic or mixed deterministic-stochastic algorithm.

Furthermore, the temporal sequences $\tau_1^{(j)}$, $\tau_2^{(j)}$, $\tau_3^{(j)}$, $\tau_4^{(j)}$, . . . can be deterministic or stochastic or mixed deterministic-stochastic. The temporal sequences $\tau_1^{(j)}$, $\tau_2^{(j)}$, $\tau_3^{(j)}$, $\tau_4^{(j)}$, . . . can in each case be uncorrelated or else statistically correlated between the different stimulation locations. Moreover, this correlation can be varied over time.

By way of example, the times $\tau_1^{(j)}$, $\tau_2^{(j)}$, $\tau_3^{(j)}$, $\tau_4^{(j)}$, . . . can be uniformly-distributed or Poisson-distributed or Gauss-distributed random processes, wherein a minimum time interval and a maximum time interval between successive macro-stimuli 30 is observed as a constraint. The random processes belonging to the respective stimulation elements j=1, 2, 3, . . . , N are uncorrelated.

It is possible for pauses to be introduced for improving the stimulation effect, e.g. according to the aforementioned k cycles ON, m cycles OFF scheme. By way of example, the non-periodic optical stimuli can be applied during k stimulation periods T. Then there is a pause of m cycles. The process is repeated thereafter.

The suitable use of appropriate individual stimuli also makes it feasible for macro-stimuli to be constructed such that temporally continuous stimuli shapes result.

According to one exemplary embodiment, half sinusoidal oscillations offset equally in time are applied over N stimulation units 11. That is to say the j-th stimulation unit 11 applies the optical stimulation signal $S_j(t)=A_j x_j(t)\theta[x_j(t)]$, wherein $A_j$ is the amplitude. $x_j(t)=\sin[\omega t+(j-1)2\pi/N]$ is the sinusoidal oscillation on which the stimulation signal is based. $\theta$ denotes the Heaviside function, i.e. $\theta[\xi]=0$ for $\xi \leq 0$ and $\theta[\xi]=1$ for $\xi>0$. The Heaviside function sets negative values of the stimulation signal to zero. j=1, 2, 3, . . . , N denotes the index belonging to the stimulation location. The amplitudes can be selected to have equal strength at all stimulation locations, i.e. $A_1=A_2=A_3= \ldots =A_N$. However, the amplitudes can also (i) be selected constant in time and varying in space or (ii) be selected to vary slowly in time according to deterministic or stochastic or mixed deterministic-stochastic algorithms.

The stimulation frequency $\omega$ can ideally be matched to the frequency of the abnormal neuronal rhythm, wherein it can however also deviate therefrom by up to ±10% or ±25% and more.

Furthermore, pauses can be introduced between the stimulation segments, e.g. completely analogously to the pulse-shaped stimulation according to the above-described k cycles ON, m cycles OFF scheme.

According to a further exemplary embodiment, the stimulation signals from the preceding exemplary embodiment are applied in each case by different subsets of stimulation units 11, but with different frequencies $\omega_1$, $\omega_2$, $\omega_3$, . . . for the respective subsets. The stimulation signals preferably have a temporally equidistant phase-shift within a subset. Then pauses can be introduced, separately (according to the k cycles ON, m cycles OFF scheme) or for all N stimulation locations, for the individual subsets.

The individual macro-stimulus does not have to be above the threshold. That is to say a macro-stimulus—dispensed on its own—does not yet have to trigger an action potential in the stimulated neuron. For the successful stimulation effect of the device according to the exemplary embodiments, it already suffices for the space-time pattern of the stimulus application to modulate the excitation threshold of the individual neurons directly or indirectly (by stimulating a supplying fiber optic) such that the overall effect is a desynchronizing effect in the neuron population. This then reduces the coincidence rate of the stimulated neuron population. As a result, abnormally stepped up synaptic connection strengths can be unlearnt, whereby this can result in a long-lasting synaptic reorganization in the involved nerve cell networks.

Figure 7:
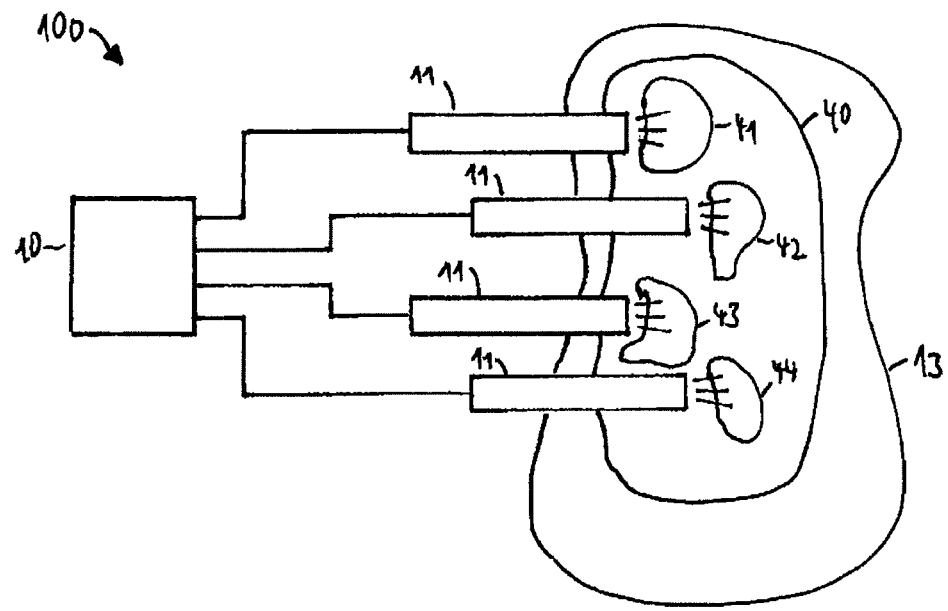
FIG. 7 shows a schematic illustration of the desynchronization of a neuron population by means of the device 100.

According to a refinement schematically illustrated in FIG. 7, optical stimuli 12 are dispensed by means of the stimulation units 11 to a neuron population 40 exhibiting an abnormally synchronous and oscillatory activity, which stimuli cause a reset of the phase of the neuronal activity of the stimulated neurons in the neuron population 40. The reset sets the phase of the stimulated neurons to a certain phase value, e.g. 0°, independently of the current phase value. Hence, the phase of the neuronal activity of the abnormal neuron population 40 is controlled by means of a targeted stimulation. Furthermore, the plurality of stimulation units 11, which can be actuated independently, allow the stimulation of the abnormal neuron population 40 at different locations. This affords the possibility of resetting the phase of the neuronal activity of the abnormal neuron population 40 at different times at the different stimulation locations. As a result, this subdivides the abnormal neuron population 40, the neurons of which were previously active in a synchronous fashion and with the same frequency and phase, into a plurality of subpopulations. FIG. 7 illustrates four such subpopulations in an exemplary fashion (this corresponds to the four illustrated stimulation units 11) and they are denoted by the reference signs 41, 42, 43 and 44. Within one subpopulation 41 to 44, the neurons are still synchronous and still fire with the same pathological frequency after the phase is reset, but each of the subpopulations 41 to 44 has the phase in respect of its neuronal activity that was imposed on it by the optical stimulation stimulus. This means that after the reset of their phases, the neuronal activities of the individual subpopulations 41 to 44 still have an oscillatory or rhythmic profile with the same pathological frequency, but different phases.

Due to the abnormal interaction between the neurons, the state with at least two subpopulations, which state was generated by the stimulation, is unstable and the entire neuron population 40 quickly approaches a state of complete desynchronization, in which the neurons fire in an uncorrelated fashion. The desired state, that is to say the complete desynchronization, thus is not available immediately after the application of the optical stimuli via the stimulation units 11, but usually sets in within a few periods or even within less than one period of the pathological frequency.

A theory for explaining the stimulation success is based on the fact that the ultimately desired desynchronization is only made possible by the abnormally increased interaction between the neurons. Hereby, a self-organization process is utilized, which is responsible for the abnormal synchronization. The same process brings about a desynchronization following a subdivision of an entire population 40 into subpopulations 41 to 44 with different phases. In contrast to this, there would not be effective desynchronization without an abnormally increased interaction of the neurons.

Moreover, the optical stimulation with the device 100 can obtain a restructuring of the connectivity of the dysfunctional neural networks and so long-lasting therapeutic effects can be brought about. The obtainable synaptic reorganization is of great importance for the effective treatment of neurological or psychiatric disorders.

The abnormal neuron population 40 and more particularly the individual subpopulations 41 to 44 can also be stimulated indirectly by the optical stimuli 12 being dispensed to nerve fibers supplying these populations. By way of example, the optical stimuli 12 can be applied at different locations in the inner ear. Here, the stimulation locations are selected such that the stimuli from the respective stimulation locations are respectively transmitted to one of the subpopulations 41 to 44 via supplying fibers.

Different approaches can be taken to obtain a desynchronization of the entire neuron population 40 by time-offset resetting of the phases of the subpopulations 41 to 44 of the abnormally synchronous neuron population 40. By way of example, optical macro-stimuli 30 can be applied via the various stimulation units 11, as described above and shown in an exemplary fashion in FIGS. 4, 5 and 6.

Figure 8:
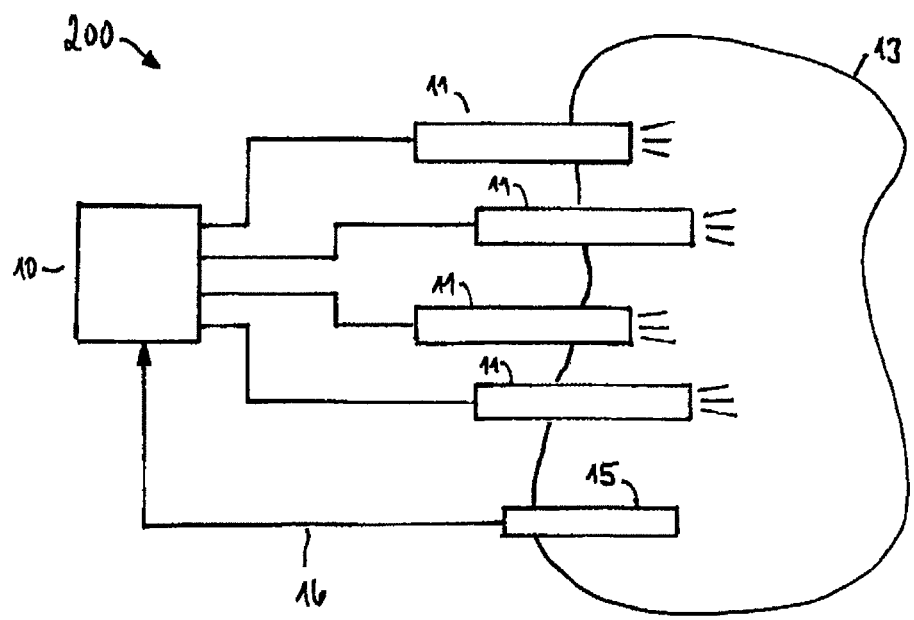
FIG. 8 shows a schematic illustration of a device 200 for optical stimulation as per an exemplary embodiment during operation.

By way of example, the device 100 can be operated in a so-called "open loop" mode, in which predetermined optical stimuli 12 are emitted to the nerve tissue by the stimulation units 11. Moreover, the device can also be developed to form the device 200 shown in FIG. 8, the latter device constituting a so-called "closed loop" system. The device 200 still additionally contains the measuring unit 15, which measures one or more measurement signals 16 in the patient and transmits said signals to the control unit 10. A demand-driven stimulation can be carried out with the aid of the measurement signals 16. The demand-driven stimulation is controlled by the control unit 10. All optical stimuli 12 described above in conjunction with the device 100 can in principle be used as optical stimulation stimuli 12.

The demand control of the stimulation brings along, inter alia, the following effects:
(i) Reduction in the energy requirement of the stimulation.
(ii) Reduction in the charge introduced and hence reduction in the side-effect rate of the stimulation.
(iii) Effective stimulation at optimally low stimulation intensity. This allows the nerve tissue in particular to resume the physiological (healthy) information processing with as little disturbance as possible and so the synaptic links required for this are reformed.
(iv) After unlearning the abnormal neuronal dynamics by means of the optical stimulation, the demand control affords a monitoring function, i.e. the stimulation is only restarted once the abnormally rhythmic neuronal activity has reformed.

The following signals can be used for the demand control:
(i) Electrical signals, which are introduced at electrical contact locations in the brain and/or spinal cord and mirror the electrical activity in the brain and/or spinal cord. The contact locations can be housed with the optical stimulation locations in a structurally unified fashion and/or can be housed in a separate electrode implanted at a different point in the brain or spinal cord. By way of example, deep brain electrodes, sub- or epidural brain electrodes, subcutaneous EEG electrodes and sub- or epidural spinal cord electrodes can serve as invasive sensors. Moreover, electrodes to be attached to peripheral nerves can be used as sensors. In addition to the invasive sensors or as an alternative thereto, it is also possible for one or more noninvasive sensors to be used, such as electroencephalography (EEG) electrodes, magnetoencephalography (MEG) sensors and electromyography (EMG) electrodes.
(ii) Signals, which are not measured in the brain, but which have a sufficiently close or causal connection to the abnormal neuronal activity, e.g. the measurement of abnormal motor activity by means of e.g. accelerometers or the measurement of vegetative parameters such as the heart rate or the skin resistance.

In order to determine the demand control, the following methods can for example be used:
(i) Univariate data analysis:
Individual signals are evaluated. By way of example, a frequency spectrum is calculated or the amplitude is determined in a certain frequency range.
(ii) Bi- and multivariate data analysis:
Single signals are not used for the control; rather, relevant quantities are determined from two or more signals. By way of example, the phase synchronization or coherence or directionality of the coupling (i.e. the strength of the influencing: which process drives the respective other process more strongly?) between two signals is determined (e.g. between a local field potential, measured by electrical contacts in the brain, and peripheral tremor activity, measured by an accelerometer).

The demand-driven switch-on of the optical stimulation can be brought about by means of one or more of the methods described in the following text:
(i) Detection of pathological activity (demand control in a narrower context):
Here, the development of the pathological feature or pathological features relevant to the disease is determined and the stimulation is initiated after a certain development, e.g. when a threshold is exceeded. An example of such a pathological feature is e.g. the amplitude of the abnormal activity in the beta-frequency range (between 13 and 30 Hz) in the case of an akinetic Parkinson's patient. The stimulation is activated when the amplitude exceeds a threshold. The stimulation is turned off again as soon as the amplitude drops below the threshold again. As an alternative to this, the stimulation can also be carried out for a minimum period of time. After this minimum period of time has elapsed, it is determined whether the amplitude has dropped below the threshold.
(ii) Detection of precursors of abnormal neuronal activity (quasi-prophylactic stimulation):
Here, dynamic processes that are precursors to disease-specific processes of the respective disease are detected. In the case of e.g. epilepsy, examples of such precursors are abnormal synchronization processes between different measurement locations in the brain, i.e. between different measurement contacts.
(iii) Detection of neuronal states in which the desynchronizing stimulation achieves particularly pronounced long-lasting therapeutic effects. The stimulation is initiated if such neuronal states are detected.

According to one embodiment of the demand-driven stimulation, the stimulation parameters are varied in a demand-driven fashion. For this, the strength of the pathological activity is detected. The extent of the pathological activity is used to control one or more stimulation parameters, e.g. the amplitude of the optical stimuli, the length of the macro-stimuli, the duration of the individual stimuli, the shape and frequency of the individual stimuli, the frequency within the macro-stimuli, the stimulation frequency at which the macro-stimuli are applied, or the pauses with which the macro-stimuli are applied within a stimulation period, etc.

Furthermore, the pauses between the applications of the optical stimuli 12 can be varied, driven by demand. When applying macro-stimuli according to the above-described k cycles ON, m cycles OFF mode, the parameters k and/or m are varied, depending on activity, as a function of the extent of the pathological activity. By way of example, the pauses (parameter m) can be lengthened when there is a reduction in the pathological activity.

Furthermore, provision can be made for demand-driven adaptation of the subset of the activated stimulation locations. The subset of the stimulation locations used for the stimulation can be varied as a function of the spatial distribution of the pathological activity. For example, this subset can be adapted such that stimulation is only effected in the region of abnormal activity.

The aforementioned stimulation modes are suitable to a different extent for individual diseases and also for individual patients. In order to optimize the therapeutic effect, the control unit 10, also matched to the individual patient, can switch from one stimulation mode to the other when required by said patient. For example, the control unit 10 can firstly select a "rigid", periodic stimulus succession as in FIG. 4 in order to suppress the abnormal symptoms as quickly as possible. As soon as the abnormal activity abates, the control unit 10 can, e.g. after a number of days, switch to the stimulation mode as in FIG. 5 for obtaining an extensive reconfiguration of abnormal synaptic networks.

Furthermore, provision can be made for measurement signals 16, which adequately represent the extent of the abnormal neuronal activity and are recorded by the measuring unit 15, to be applied directly or possibly after one or more processing steps as optical stimulation stimuli 14 by the stimulation units 11 (feedback stimulation method). The measuring units mentioned above in the context of the demand control can be used as measuring units 15. An individual measurement signal 16 or a plurality of measurement signals 16, after being combined linearly or nonlinearly, is or are applied via all stimulation locations or via a subset of stimulation locations. As an alternative to this, the stimulation signal can also be applied via the individual stimulation locations with a time delay or with a phase shift.

In the case where the measurement signals 16 recorded in the patient are fed back into the body of the patient, the device 200 does not necessarily have to contain a plurality of stimulation units 11, in principle only one stimulation unit 11 could suffice.

In the case of linear processing of the measurement signals 16, the latter can for example be filtered and/or amplified and/or actuated with a time delay, before the signals processed in this fashion are dispensed with the aid of the stimulation units 11. The following text, with the aid of examples, explains how optical stimulation stimuli 12 can be generated from the measurement signals 16 by linear or nonlinear processing.

(i) Example 1

A local field potential is measured, amplified, band-pass filtered for extracting the relevant pathological activity and set to zero wherever the values thereof are negative. The signal preprocessed in this fashion is applied via the j-th stimulation location with a time delay of $\Delta t+(j-1)T/M$ (i.e. the laser amplitude is, for example, modulated by this signal), wherein a total of M different stimulation locations (=stimulation units 11) are used; $\Delta t$ denotes a time delay that can be matched to the individual patient for obtaining the optimum stimulation effect and T is the stimulation period.

(ii) Example 2

A local field potential $x(t)$ is measured, amplified and band-pass filtered for extracting the relevant pathological activity. Next, the complex analytic signal $z(t)$ belonging to $x(t)$ is formed. From this, the stimulation signal $S_1(t)=Cz^2(t)z^*(t-\tau)$ is formed. Herein, C is an amplification factor, $\tau$ is a time delay, which can e.g. be selected in the region of half the average period of the abnormal oscillatory activity; however, due to the particular selection of the stimulation signal, the stimulation is also effective (in the sense of a desynchronization of the abnormal neuronal synchronous activity) for other values and more particularly for almost the entire range from e.g. a quarter to three times and more of the average period of the abnormal oscillatory activity. Wherever this stimulation signal has negative values, these are set to zero, i.e. this results in the stimulation signal $S_2(t)=\theta[S_1(t)]$. $\theta$ denotes the Heaviside function, i.e. $\theta[\xi]=0$ for and $\xi\leq0$ and $\theta[\xi]=1$ for $\xi>0$. The stimulation signal $S_2(t)$ is applied via all stimulation locations. As an alternative to this, it is also possible for different time delays to be selected for different stimulation locations.

(iii) Example 3

Instead of the nonlinear stimulation signal $S_1(t)$ from the aforementioned example 2, a proportional-integral-derivative (PID) feedback can also be used and—as explained with reference to example 2—continue to be used (i.e. all negative values of $S_1(t)$ are set to zero).

(iv) Example 4

Stimulation signals are calculated as explained in the examples above from two or more different regions of the brain, which regions are respectively acquired by a subset of stimulation locations and the associated neuronal activity of which is registered by measuring contacts. However, unlike the aforementioned examples, these stimulation signals are then not applied in the region of origin via the stimulation locations, but they are applied at a different location. Here, different combinations, which can in each case be automatically tested by the control unit 10, can be found to be particularly effective.

The devices 100 and 200 can be used successfully, inter alia, in the case of the diseases listed below, wherein examples for effective target points (TP) are mentioned within parentheses following the respective disorders:

Neurological Disorders:

Parkinson's disease (TP: subthalamic nucleus (STN), ventrointermediate (VIM) nucleus of the thalamus and subthalamic fiber bundles lying therebelow, internal globus pallidus), essential tremor (TP: VIM and subthalamic fibers), dystonia (TP: internal globus pallidus), spasticity (TP: subthalamic nucleus, ventrointermediate (VIM) nucleus of the thalamus and subthalamic fiber bundles lying therebelow, internal globus pallidus), tremor in a condition after concussion (TP: VIM and subthalamic fiber bundles lying therebelow, STN), epilepsy (TP: STN, vagus nerve, epileptic foci inter alia in the cortex, hippocampus), Alzheimer's disease (TP: hippocampus, nucleus basalis of Meynert), spinocerebellar ataxia (TP: ventrointermediate (VIM) nucleus of the thalamus and subthalamic fiber bundles lying therebelow), pain therapy (TP: thalamus, motor cortex) and cluster headache.

Psychiatric Disorders:

Depression (TP: nucleus accumbens, subgenual cingulate [Cg25], inferior thalamic peduncle, lateral habenula, vagus nerve), obsessive disorders (TP: nucleus accumbens, inferior thalamic peduncle) and Tourette's syndrome (TP: centromedian-parafascicular and ventral-oral complex of the thalamus, periventricular substance, nucleus accumbens, internal capsule, internal globus pallidus).

The light stimulation by means of the devices 100 and 200 requires the use of a light source with sufficient energy and suitable signal shape. By way of example, (e.g. tunable) lasers with wavelengths in the region of 1 to 1.6 µm and an energy between 200 µJ and 5 mJ, or pulsed lasers with wavelengths between 1 and 8 µm and pulse energies between 150 µJ and 5 mJ are suitable for triggering action potentials when impinging on nerve tissues. These lasers are still comparatively large and can currently only be used outside of the body. However, it is expected that laser development, particularly in the field of diode lasers, affords such small equipment in the near future that these lasers can also be used within the body as implants. However, the modulation of individual neuron populations according to the exemplary embodiments does not necessarily require the triggering of action potentials. Rather, the corresponding neuron populations can also be sensitized by below-threshold stimulation. For this, other light sources, such as light-emitting diodes (LED), can be used in addition to lasers and laser diodes.

Suitable components are then used to couple the light into one or more light-conducting fibers, which can be combined as a fiber bundle. Corresponding components are presented below.

The advantage of the below-threshold stimulation is that the laser energy can be selected to be relatively low and the risk of tissue damage as a result of pulse energies that are too high or light energy that acts for too long does not apply.

Light-conducting fibers and fiber bundles can be produced to be very thin and so it is possible for a target area to be entered by very many fibers (e.g. more than one hundred or even many hundred fibers). Compact arrangements for decoupling the light are also illustrated below, which arrangements permit a large number of contact points of the light emission with the target area. A large number of contact points is of great interest, particularly in desynchronizing stimulation methods and feedback stimulation methods, because a large number of contact points in these methods allows a particularly efficient therapeutic reconfiguration of the affected nerve networks.

When certain wavelengths are selected, the penetration depth of the light can additionally be selected to be much smaller than the extent of conventional current distributions in the case of electrical stimulation. This affords a more precise spatial delimitation of the stimulation effect. More particularly, the light stimulation does not require a counter-electrode either and so the effect can in fact be restricted to a defined location.

Since the light stimulation does not cause a flow of electric charge, electric deductions of brainwaves or potentials can be brought about at the same time as the stimulation without mutual interference. The advantage of this is that deductions, i.e. the recording of the measurement signals 16, can be effected continuously, even during the stimulation. More particularly, this does not result in the creation of dead times if the deduced signals should be used directly or after further processing as feedback signals, i.e. as stimulation signals.

During the light stimulation, no charges are transported into the tissue or the cells. Accordingly, no complex measures or electrical circuits are required for charge balancing. Charge balancing means that, within short time intervals, just as much charge flows into the target area as flows out therefrom. Such charge balancing is problematic in the case of continuous electrical signals. Accordingly, the light stimulation is very advantageous for feedback-stimulation methods, in which it is desirable to use continuous stimulation signals.

Since the light-conducting fibers made of glass or plastic can be produced without any metal, they are neither electrically conductive nor magnetic. Accordingly, the light stimulation can be brought about at the same time as imaging or diagnostic methods such as magnetoencephalography (MEG), electroencephalography (EEG) and magnetic resonance imaging (MRI) without mutual interference.

In the following text, exemplary embodiments for the devices 100 and 200 are presented. Individual features mentioned in the context of certain exemplary embodiments can also be combined with other exemplary embodiments.

Figure 9:
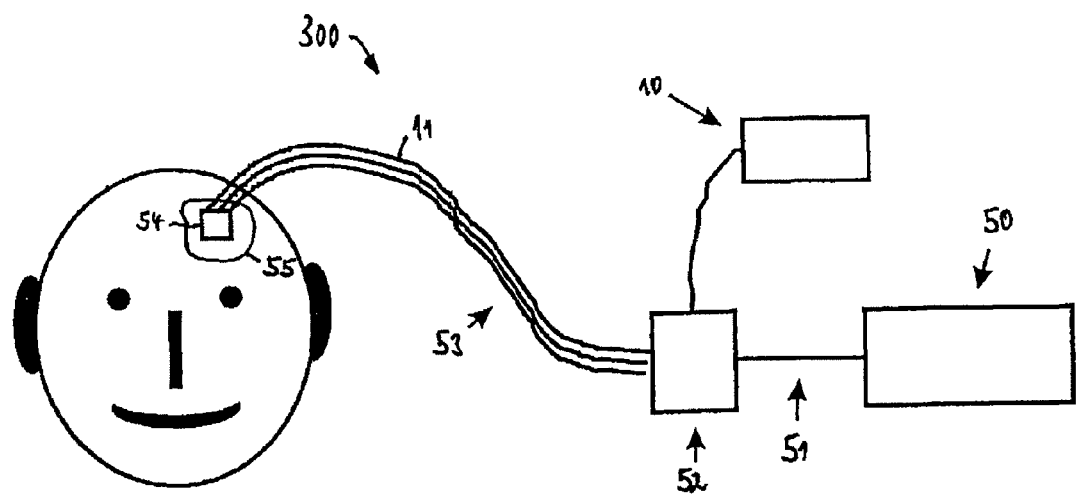
FIG. 9 shows a schematic illustration of a device 300 for optical stimulation as per an exemplary embodiment during operation.

FIG. 9 illustrates a device 300 as an exemplary embodiment. A light source 50, which can be a laser, a laser diode, an LED or another light source, is used to generate a light beam 51, which, with the aid of a flexible light coupling 52, is distributed over a plurality of inputs of a fiber bundle 53 consisting of a plurality of optical guides 11. In the process, a control unit 10 determines at what time the light, an individual light pulse or a train of light pulses is coupled into which fiber 11 of the fiber bundle 53. The decoupling points 54 of the individual fibers 11 of the fiber bundle 53, i.e. the ends of the fibers 11, lie at different points in the target area 55, in this case an area in the brain. Thus, the light stimulates different locations of the target area 55 in a temporal sequence determined by the control unit 10.

Figure 10:
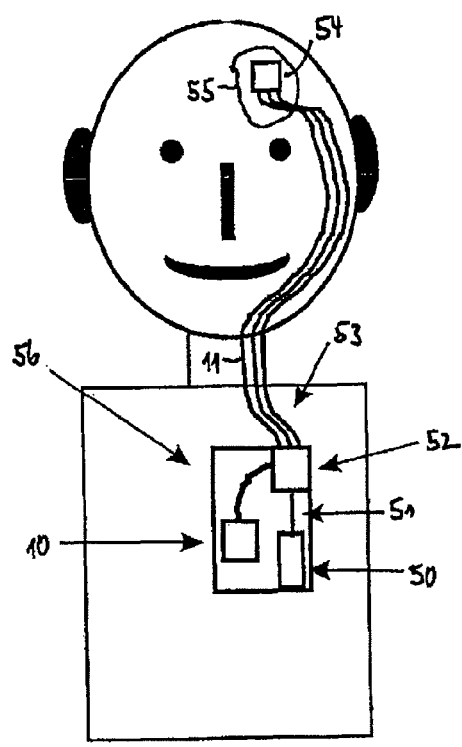
FIG. 10 shows a schematic illustration of the device 300 as a complete implant.

FIG. 10 shows the device 300 in a form in which the light source 50, the fiber coupling 52 and the control unit 10 are located in the body of the patient as implanted equipment. In this refinement, it is expedient for the light source 50, the light coupling 52 and the control unit 10 to be housed in a common implantable housing 56 with a connector for the fiber bundle 53.

It is expedient that light from the light source 50 is coupled into one or more light-conducting fibers 11. In the process, it is also possible for a light beam to be distributed amongst a plurality of adjacent thin fibers 11, which then transport the light together. In the following text, different components for achieving these objects are presented.

Figure 11:
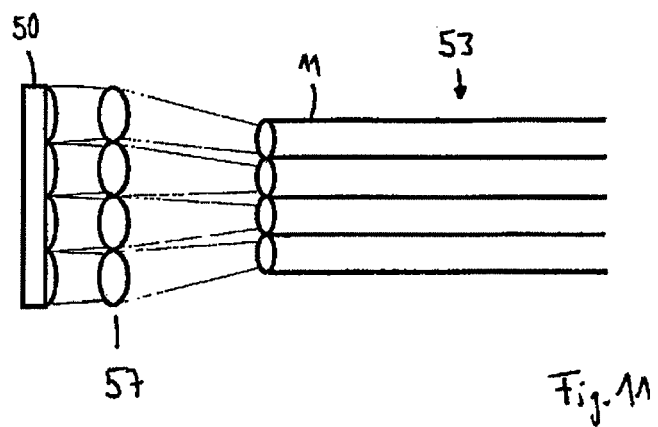
FIGS. 11 to 17 show schematic illustrations of different refinements for coupling optical stimuli into optical fibers.

In a first embodiment, the light can be distributed to a plurality of fibers 11 of a fiber bundle 53 by the use of a light source 50 emitting a plurality of beams or an array of light sources 50 such as an LED array. FIG. 11 shows a schematic arrangement of this coupling-in variant. Expediently, use can additionally be made of a micro-lens array 57 in order to image the beams of the LED array 50 on the entry pupils of the fiber bundle 53. To make the illustration simpler, the LED array 50, the micro-lens array 57 and the fiber bundle 53 are only illustrated in the plane of the paper in FIG. 11. It goes without saying that the coupling-in can also be effected in a plane.

Figure 12:
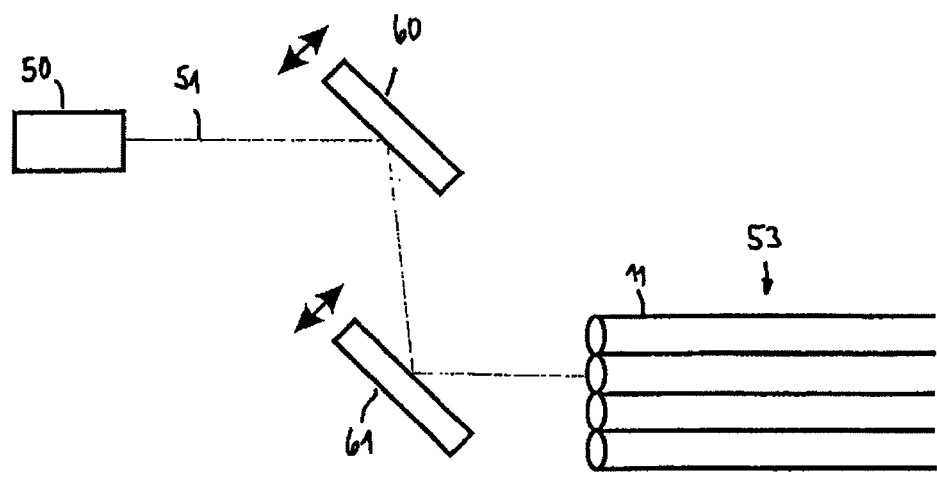

FIG. 12 shows a second embodiment of a light coupling into a fiber bundle 53. In this example, the light beam 51 of a light source 50 is guided into the individual fibers 11 of the fiber bundle 53 via two-dimensional deflection by means of two tiltable mirrors 60 and 61. Depending on the alignment of the two mirrors 60, 61, which can be tilted about different axes, the input of a different fiber 11 is hit and the light is coupled into the latter. Here, the mirrors 60, 61 can be tilted by means of different drives such as piezo-actuators. The mirrors 60, 61 can furthermore be tilted about different axes and so two-dimensional movement is possible. For reasons of simplicity, this variant was not illustrated in FIG. 12.

It is also possible to use a single, flexibly suspended mirror or mirror array instead of using two mirrors.

Figure 13:
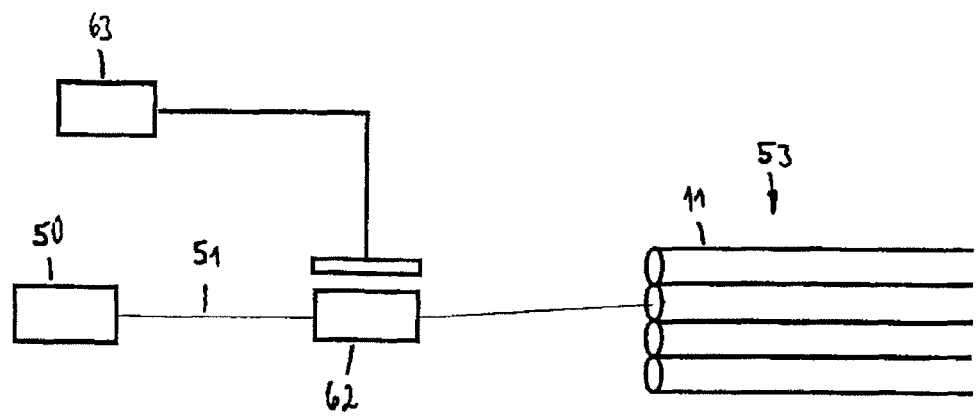

A further embodiment is illustrated schematically in FIG. 13. Here, use is made of an electro-optical component 62 that can cause a deflection of an entering light beam 51. The electro-optical component 62 can be e.g. an acousto-optical modulator (AOM). In the medium of the latter, a standing acoustic wave is generated by applying a high-frequency voltage signal from a signal generator 63, which standing wave is able to bend the light into a certain direction.

Other refinements of the light coupling-in are also feasible. By way of example, the fiber bundle 53 itself can be moved in two dimensions and so the light beam 51 reaches a different fiber 11 depending on the position of the fiber bundle 53.

In each of the mentioned embodiments, the pulsed or not-pulsed light from a light source 50 (laser, laser diode, LED or other) is distributed over many fibers 11. In principle, it is possible for the light to be distributed over an arbitrary number of fibers 11 (e.g. 1 to 100) with an arbitrary distribution. Since these fibers 11 can be positioned differently in the target tissue, this accordingly allows a very high spatial resolution of the light stimulation.

Figure 14:
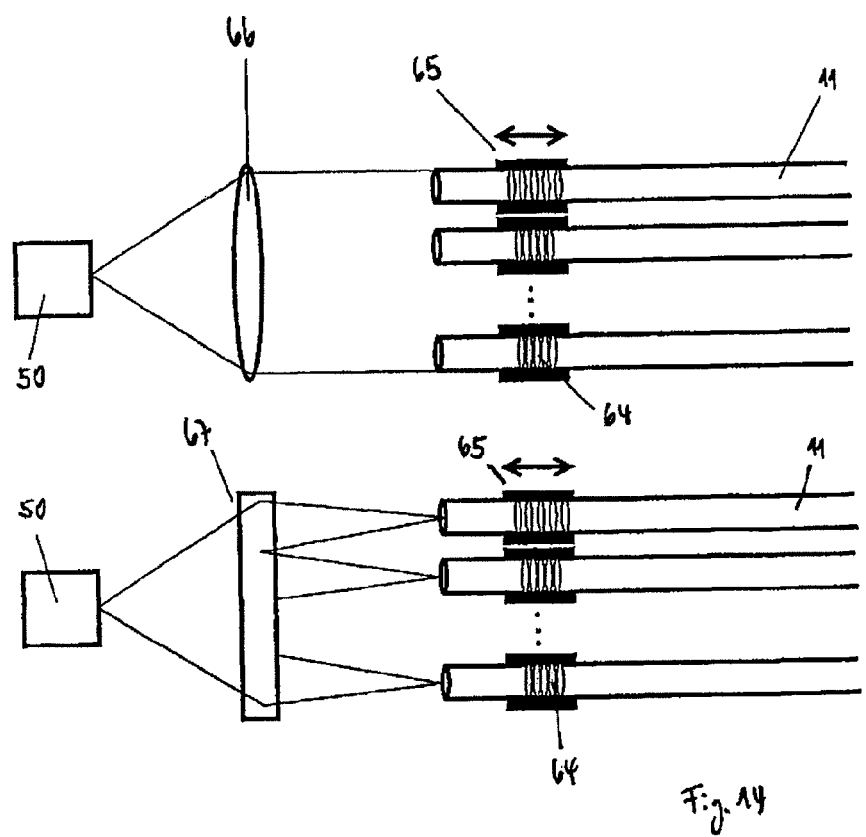
Figure 15:
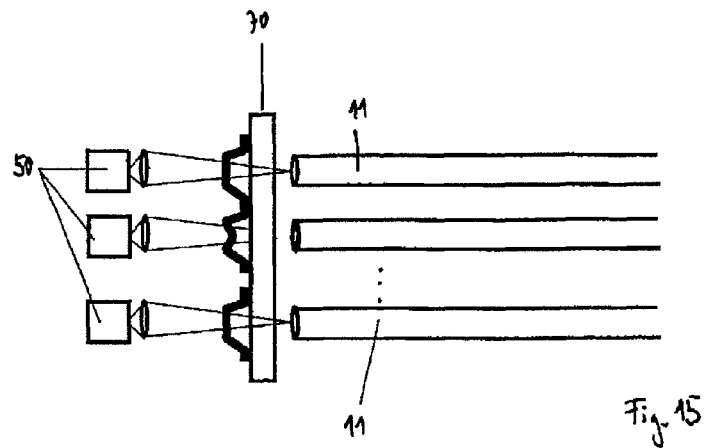
Figure 16:
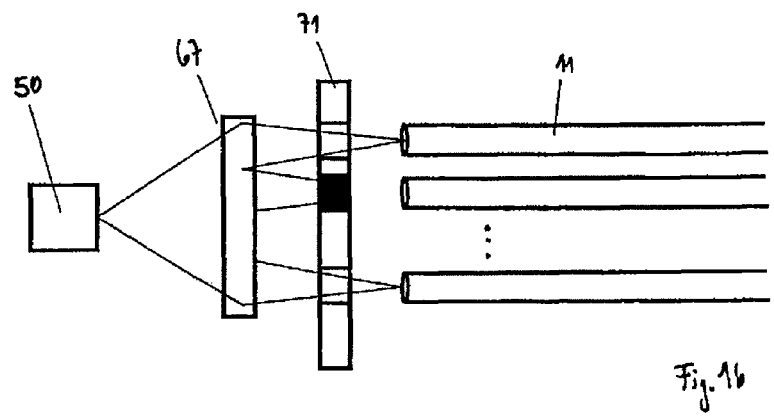

FIGS. 14 to 16 show embodiments in which the light of the light source 50 is imaged onto the inputs of many fibers 11 by means of a suitable optical system. Using the devices described in the following text, it is possible for the light to pass through only certain predetermined fibers 11 in a selective fashion.

FIG. 14 shows two refinements of an "embedded grating" stimulator. Here, the transmission of the optical fibers 11 is modulated by integrated, variable gratings 64. The gratings 64 consist of grids, the spacing of which can be varied. Depending on the spacing of the grids from one another, this results in constructive or destructive interference, which allows or prevents the transmission of the light through the respective fiber 11. The spacing variation of the grids is brought about by a mechanical (piezo) or thermal actuator 65. In the upper refinement shown in FIG. 14, the light generated by the light source 50 is fed into the fibers 11 by means of a refractive coupling optical system 66, whereas the lower refinement makes use of a diffractive coupling optical system 67.

FIG. 15 schematically shows a refinement of a "Fabry-Perot switch" stimulator. The light is coupled into the optical fibers 11 by variable Fabry-Perot cavities of a Fabry-Perot array 70. The Fabry-Perot cavities are modulated by deformable membranes. Depending on the deformation of the respective membrane, there is light transmission or the latter is prevented. Fabry-Perot switches can be obtained integrated in MEMS (micro-electromechanical system) form.

FIG. 16 schematically shows a refinement of a DOE (diffractive optical element) stimulator. The light is coupled into the optical fibers 11 by a fan-out DOE 67 and a light modulator 71. By way of example, the light modulator 71 can be designed as a liquid-crystal shutter, which permits selective transmission.

Figure 17:
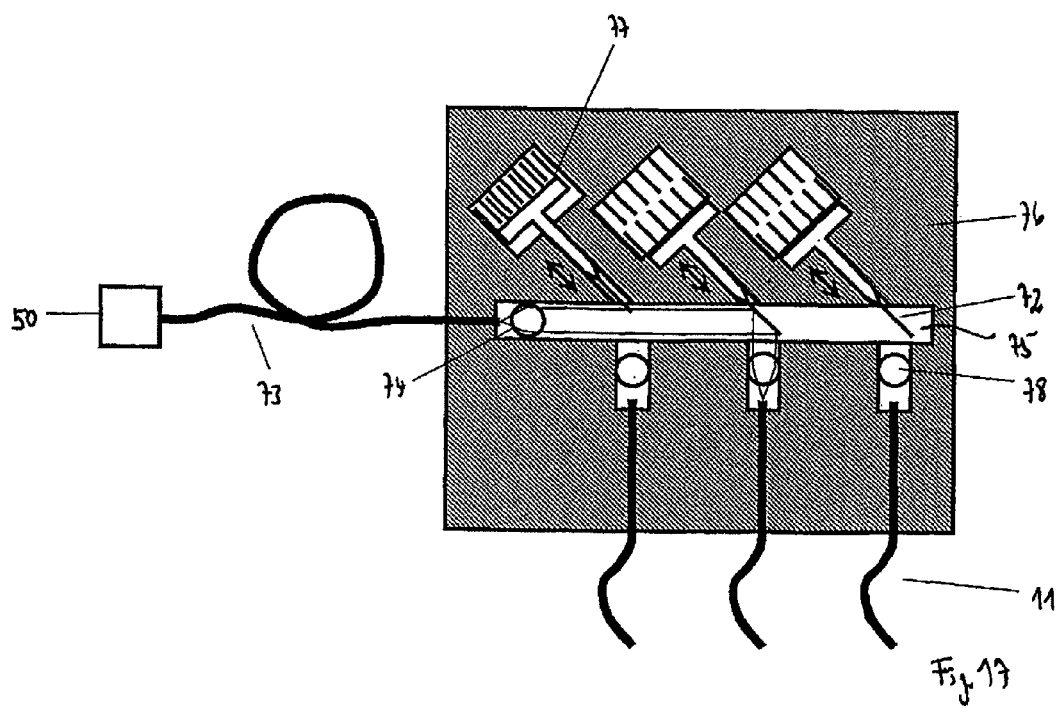

FIG. 17 schematically shows a refinement of a "MEMS optical shutter" stimulator. The coupling of the light into the optical fibers 11 is modulated by micro-mechanically actuated deflection mirrors 72. Here, the light of a light source 50 is introduced into a channel 75 in a semiconductor chip 76 via an optical fiber 73 and a collimator 74. Actuators 77 can move the deflection mirrors 72 and accordingly feed the light into the desired fibers 11. Furthermore, a coupling optical system 78 is in each case arranged upstream of the fibers 11.

Figure 18A:
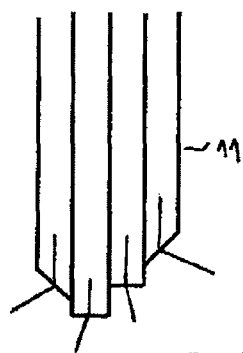
FIGS. 18A to 18D, 19A to 19C, 20A to 20B, and 21 show schematic illustrations of different refinements for coupling optical stimuli out of optical fibers.
Figure 18B:
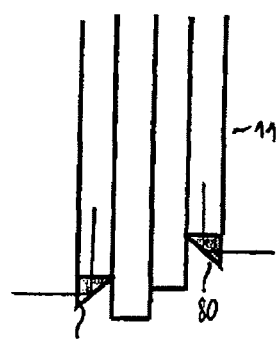

The light emanating from the fiber 11 or the fiber bundle 53 can be guided to certain locations in the target area in different fashions. In the following text, a few exemplary embodiments, illustrated schematically in FIGS. 18A to 18B, are explained with respect thereto.

Figure 18C:
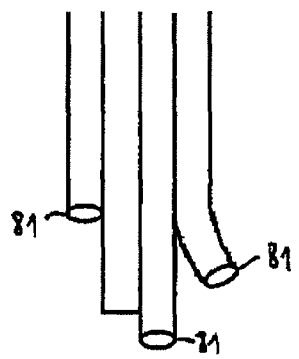
Figure 18D:
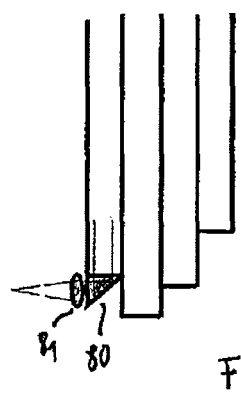

The light emission ends of the individual fibers 11 of the fiber bundle 53 can be shaped (cf. FIG. 18A) by polishing, other mechanical processing, chemical processing or fusing, or can be expanded by applying miniaturized prisms 80 (cf. FIG. 18B) such that the light is no longer emitted forward, but at different angles to the side. This allows the stimulation to be undertaken in lateral directions in a very targeted fashion. Additionally, it is possible to shape the fiber ends such that they form a lens 81 and so the emanating beam of light is focused at a predetermined working distance (cf. FIG. 18C). As a result, this focusing can also be implemented by applying a miniaturized lens 81 directly in front of the light emission end or the additionally applied prism 80 (cf. FIG. 18D).

It goes without say that it is also possible to combine a plurality of fibers 11 of the fiber bundle 53 and deflect the light from all fibers 11 together in a certain direction and/or to focus said light. Moreover, it is possible to detach individual fibers 11 from the fiber bundle 53 and to guide them in another direction (cf. FIG. 18C).

Figure 19A:
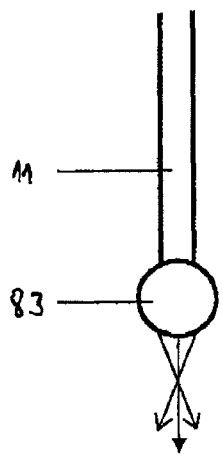
Figure 19B:
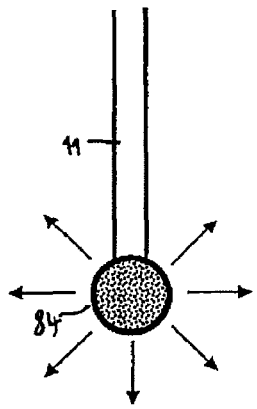
Figure 19C:
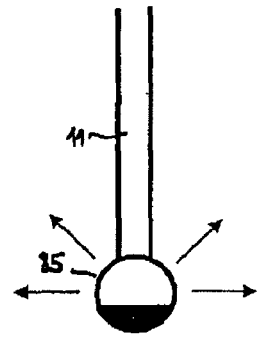

It is also possible to integrate passive elements into the optical fiber 11 at the optical fiber end, which elements deflect the light in the desired directions. For example, FIG. 19A shows integrated into the optical fiber 11 a lens 83 for focusing the light, FIG. 19B shows an isotropic diffuser 84, which is produced by e.g. roughening the surface of the sphere arranged at the end of the fiber, and FIG. 19C shows an anisotropic reflector/diffuser 85. Here, the reflector is implemented by partial mirroring.

The light can also be distributed to various locations by other means: etching, mechanical roughening or other methods allow the treatment of an individual light-conducting fiber 11 such that light can only be emitted at the affected surfaces. This allows the implementation of e.g. punctiform, rectangular or annular emanating points.

Figure 20A:
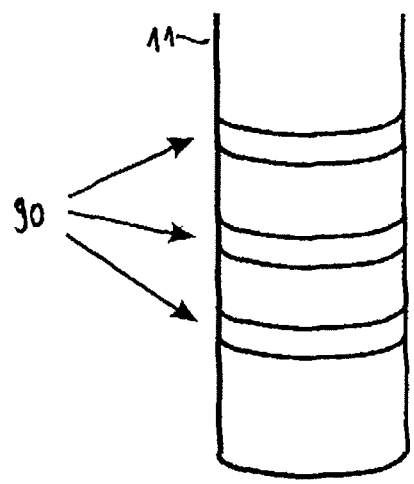
Figure 20B:
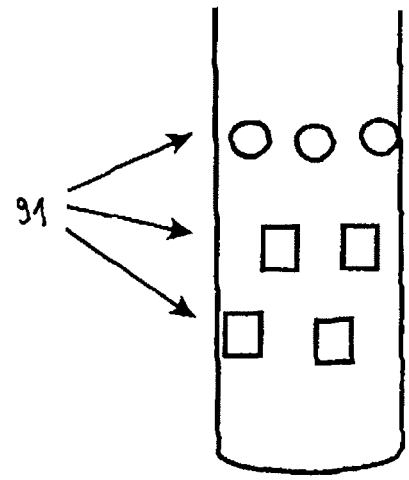

FIG. 20A shows an exemplary embodiment in which an individual fiber was treated such that the light emanates laterally from three processed rings. FIG. 20B shows an exemplary embodiment with individual light emission points and light emission rectangles 91, which can be placed on the fiber 11 in an arbitrary arrangement.

It goes without saying that other forms of roughening or etching than the illustrated forms are also possible. It goes without saying that it is also possible to treat individual fibers 11 of a fiber bundle 53 using the above-described methods.

Figure 21:
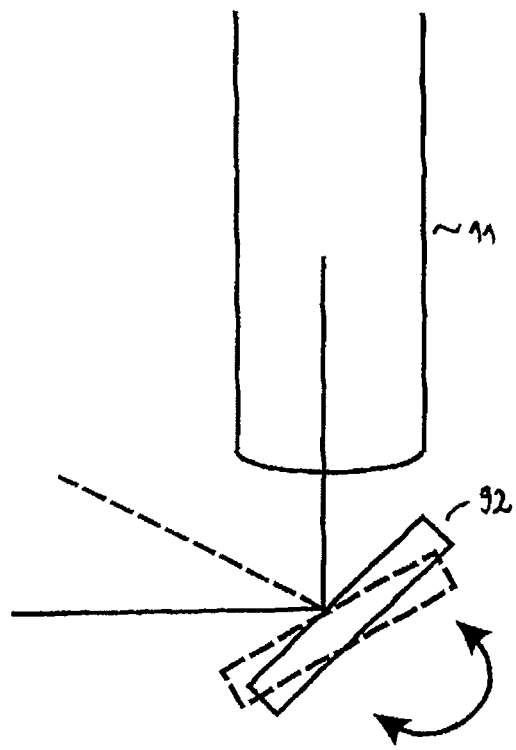

Furthermore, it is possible to apply a micro tilt mirror 92, as shown in FIG. 21, to the end of the fiber bundle 53 or an individual fiber 11, which mirror is able to direct in various directions the light emanating from the fiber bundle 53 or the individual fiber 11 in a controllable fashion. By way of example, the tilt mirror 92 can be moved about 2 axes and so the light can be directed in all directions. The tilt mirror 92 can be installed in a housing made of biocompatible material.

Figure 22:
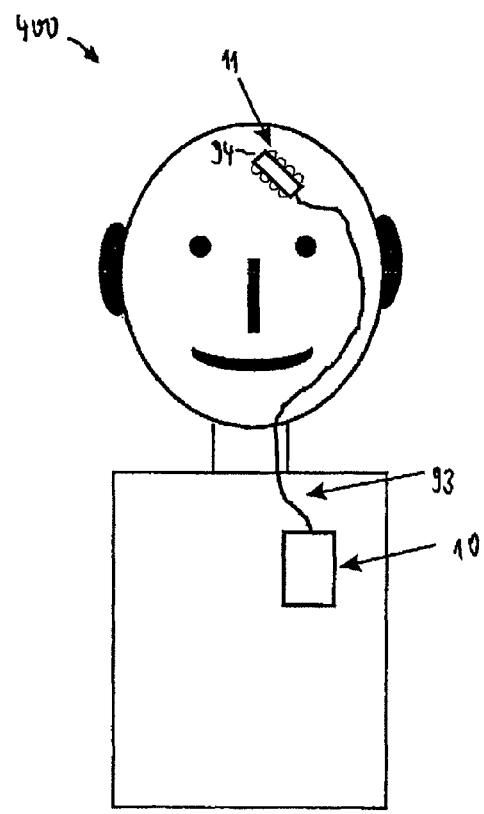
FIG. 22 shows a schematic illustration of a device 400 for optical stimulation as per an exemplary embodiment during operation.

Embodiments in which the guiding of light by means of fibers or fiber bundles is dispensed with are also feasible. Here, the signal is firstly transmitted by electrical means into the target area, in which there are individual light sources 11, e.g. LEDs. A device 400 as an exemplary embodiment of this variant is shown schematically in FIG. 22. The signal from the implanted control unit 10 is guided by means of an electric line 93 into the target area, where individual light sources 11 are located and attached in a suitable arrangement, e.g. a plastic-encased probe 94. The number and positioning of the light sources 11 can be arranged in a number of ways.

This refinement can also be arranged such that individual components are located outside of the body of the patient.

Different options for generating pulsed light or arbitrarily shaped pulse trains can be used in all the aforementioned refinements.

Figure 23:
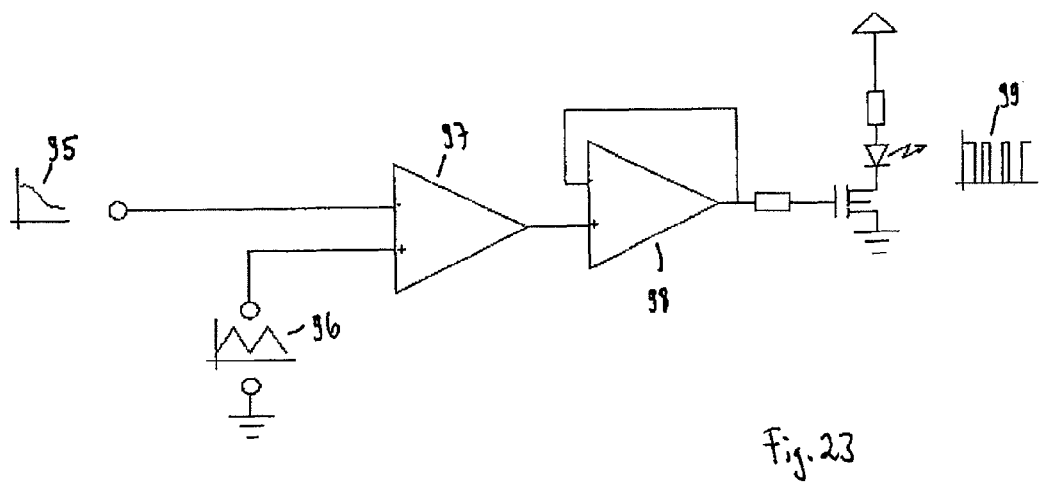
FIG. 23 shows a schematic illustration of a circuit for pulse-width modulation of optical stimuli.

First of all, it is possible to make a laser diode or an LED emit pulsed light by means of electrical actuation. This can be brought about by means of a simple linear amplitude control, in which the amount of light is directly controlled by the current. However, the amount of light can also be controlled by different forms of pulse-width modulation. Here, the amount of light is controlled with a high frequency via the ratio of the duration of being switched on and off. This is not possible by simple current actuation due to the nonlinear relationship between current and emitted light power. An exemplary embodiment of a circuit that implements a pulse-width modulation is reproduced in FIG. 23. The input modulation signal 95 is for example compared to a triangle signal 96 in a comparator 97 and is subsequently amplified by an amplifier 98. The output signal 99 is "high" and the light is "off" if the modulation signal 95 lies below the triangle signal 96, otherwise it is "low" and the light is "on". This can for example also avoid the problem of the current dependence of the emission wavelength of a laser diode or an LED.

Figure 24:
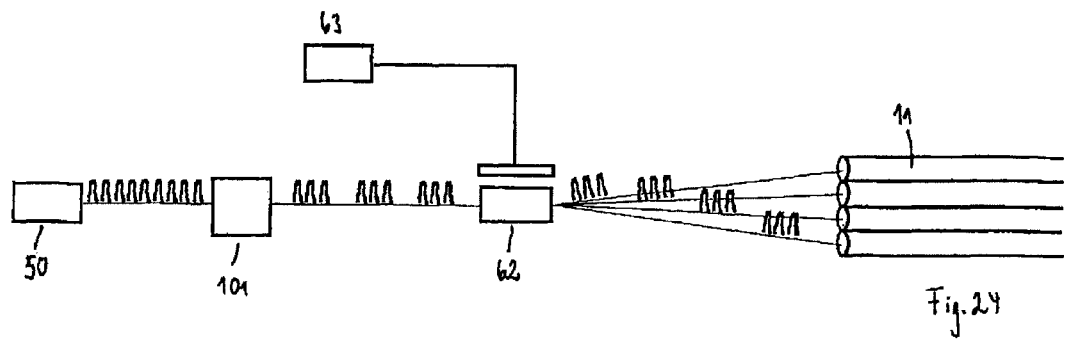
FIG. 24 shows a schematic illustration of a distribution of light pulses to different optical fibers.

Finally, there are various options for picking out individual pulses or pulse trains with arbitrary length and arrangement of the individual pulses from a continuous wave or pulsed beam of a light source by means of electro-optical elements (circuits, modulators) such as Pockels cells, liquid crystals, nonlinear crystals or acousto-optical modulators. Such elements are occasionally referred to as "pulse pickers". FIG. 24 shows a schematic illustration of an exemplary stimulation form. Here, the light is distributed amongst the inputs of four light-conducting fibers 11 with the aid of a pulse picker 101 such that three successive light pulses are transported in each fiber 11 with a time interval. If the contact points of the fibers 11 are now distributed in the target area at different locations in the target area in one of the manners described above, this results in a stimulation as shown in FIG. 7.

Figure 25:
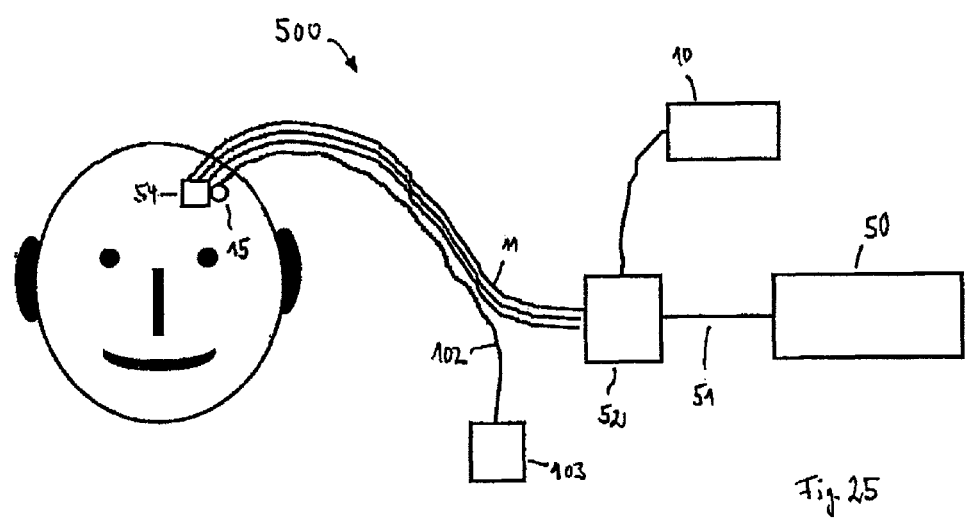
FIG. 25 shows a schematic illustration of a device 500 for optical stimulation as per an exemplary embodiment during operation.

Each of the above-described exemplary embodiments can be extended by the light stimulation being combined with an electrical deduction. FIG. 25 shows an example in which a potential recorder is positioned in the target area as a measuring unit 15, which guides the measurement signal 16 via an electrical cable 102 to recording equipment 103, where the signal can be processed, displayed and evaluated. Furthermore, the recording equipment 103 can be connected to the control unit 10.

It goes without saying that the additional electrical deduction can also be implemented by an arrangement of implants within the body.

The light stimulation and the electrical deduction can be skillfully combined with one another such that the electrical conduction required for the deduction can be performed by electrical conductors worked into the fibers or laid along the fibers. By way of example, the electrical conductors can surround individual fibers in an annular fashion and open into a deduction electrode at the end of the fiber. This only requires a single access to the target area.

However, the combination can also be designed such that separate deductions are undertaken at individual light emission points. If desired, this spatially-resolved measurement can allow each location to obtain its own feedback signal and e.g. the light stimulation is brought about at a location such that the neuron activity is controlled to the "zero potential" at this location.

However, in addition to the stimulation in the brain, the above-described electrical stimulation methods are also used in the spinal cord, for example for the treatment or alleviation of chronic pain. It goes without saying that the device according to the exemplary embodiments can also be used for stimulating nerve fibers in the spinal cord or in other body regions.

Light sources and waveguides can be formed not only as punctiform sources, but also as areal or spatial sources. The exemplary embodiments are not restricted to punctiform sources. By way of example, it can be expedient to perform an areal stimulation on the cortex. By way of example, this can be brought about by LED arrays designed as mats, which are attached along the cortex.

Figure 26:
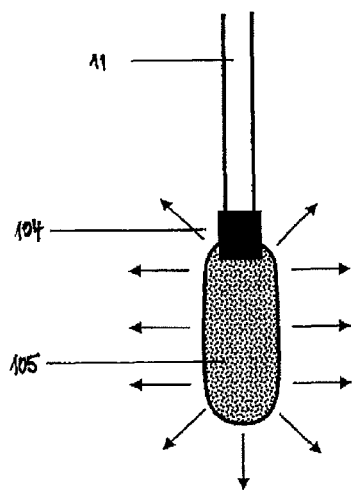
FIG. 26 shows a schematic illustration of a stimulation unit for large-area optical stimulation.

As an example for an areal stimulation, FIG. 26 shows an optical fiber 11 with a so-called light pipe 105 being attached to the end of the fiber by means of an optical connector 104. The light pipe 105 can have any geometric shape and allows an areal emission of the light fed in.

Light of certain wavelengths, e.g. near infrared, can also pass a certain distance through organic tissue. Hence, it is feasible that e.g. the cortex is also stimulated by light sources or waveguides being positioned outside of the meninges and the stimulation being brought about through the meninges. Trans-cranial stimulation is also possible in the case where only very small amounts of light are required. Of course, such a procedure is less invasive.

Figure 27:
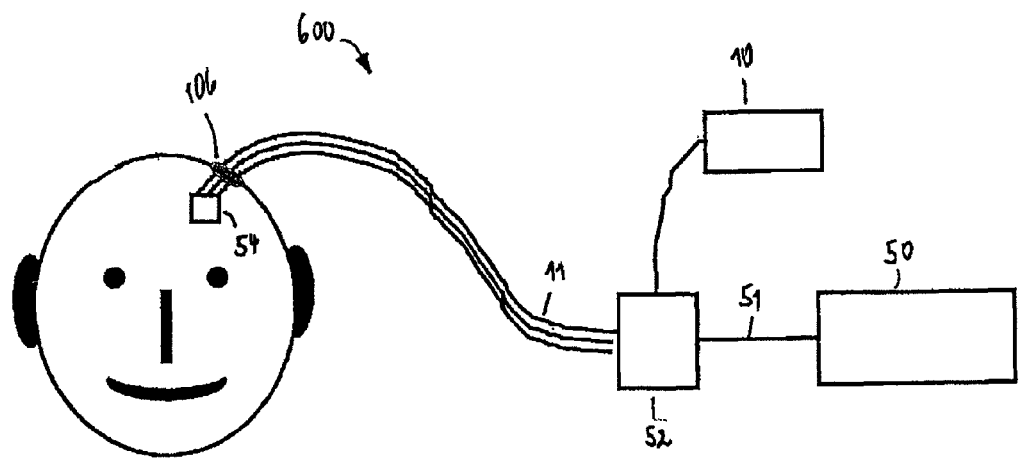
FIG. 27 shows a schematic illustration of a device 600 for optical stimulation as per an exemplary embodiment during operation.

Particularly in cases where continuous stimulation is not necessary, it can be expedient to apply a fiber coupler to an easily accessible place on the body, to which coupler an external fiber or an external fiber bundle can be applied on an outpatient basis. Then, a fiber or a fiber bundle still remains implanted in the patient. However, stimulation is then only brought about when the external equipment is connected. FIG. 27 shows this situation with a fiber coupler 106 on the cranial bone.

Figure 28:
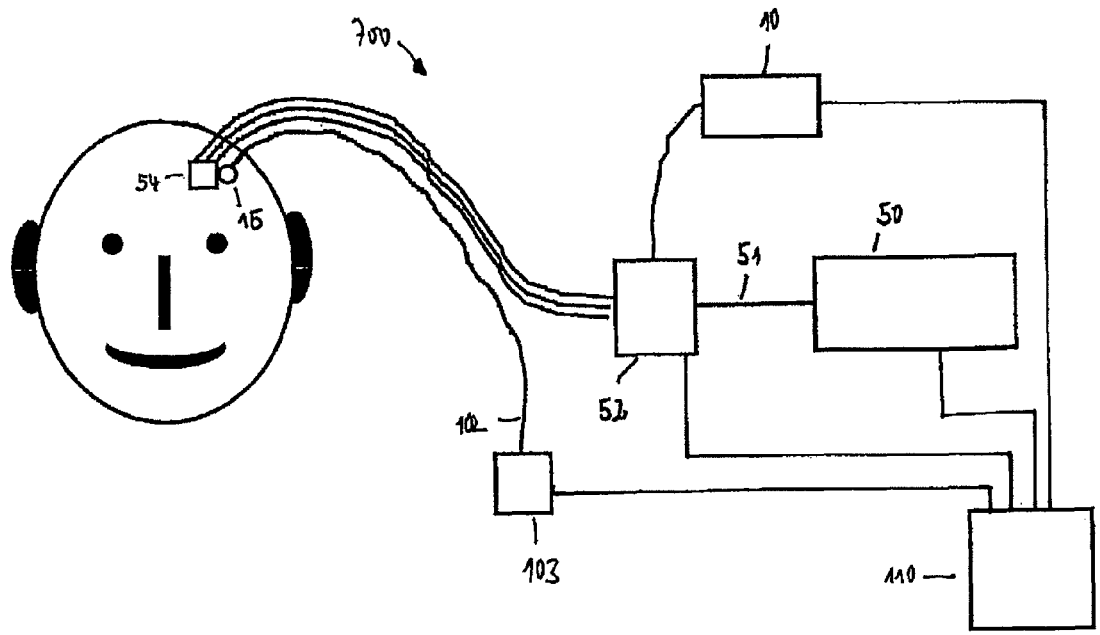
FIG. 28 shows a schematic illustration of a device 700 for optical stimulation as per an exemplary embodiment during operation.

As already illustrated in the previous discussions, the methods of the pulse selection can be combined with the methods of fiber coupling-in in various ways and so it is possible to distribute different pulse trains to different fibers. Likewise, different combinations with electrical deductions and the use of the deducted signals for generating new stimulation signals are possible. All the aforementioned methods can expediently be combined with one another such that a control can define in which temporal sequence which light signal sequences should emanate at which location in the target area at the corresponding contact points. This control possibly uses information from the deducted signals. FIG. 28 shows an exemplary embodiment in which a correspondingly designed control unit 110 is used. The illustrated device 700 is a development of the device 500 shown in FIG. 25. The control unit 110 synchronizes the functions of the individual components. It goes without saying that this example can also be designed such that the entire device is located in the body of the patient as an implant. Interactions with external control equipment are then additionally possible over wireless connections.

Figure 29:
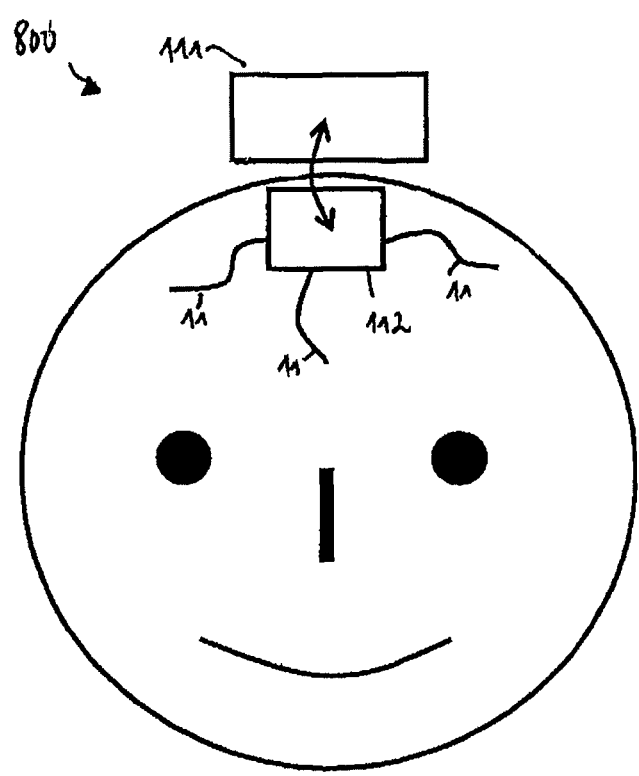
FIG. 29 shows a schematic illustration of a device 800 for optical stimulation as per an exemplary embodiment during operation.

FIG. 29 schematically shows a semi-implant 800 for optical stimulation. External equipment 111 not implanted into the body of the patient is used for generating stimulation signals and feeding the stimulation signals into the implant 112. Signals can be transmitted between the external equipment 111 and the implant 112 in a transcutaneous and bidirectional fashion, for example in an optical and/or inductive fashion. The implant 112 generates the optical stimuli 12, which are brought to their target locations by the optical fibers 11.

What is claimed is:
1. A device for resetting phases of neuronal activity, the device comprising:
   a control unit; and
   a plurality of stimulation units electrically coupled to the control unit and configured to be implanted in the body of the patient and to generate optical stimuli to stimulate neurons at a plurality of respective stimulation locations, wherein the optical stimuli reset the phases of the neuronal activity of the neurons during the direct stimulation of the neurons exhibiting abnormally synchronous and oscillatory neuronal activity, wherein the control unit is configured to actuate the stimulation units such that at least two of the plurality of stimulation units reset the phases of the respectively stimulated neurons at different times, wherein the number of stimulation units is N, wherein the j-th stimulation unit applies an optical stimulation signal $S_j(t)=A_j x_j(t)\theta[x_j(t)]$ to the respective stimulation location, with $j=1, 2, \ldots, N$ and $x_j(t)=\sin[\omega t+(j-1)2\pi/N]$ and $\theta[x_j(t)]=0$ for $x_j(t)\leq 0$ and $\theta[x_j(t)]=1$ for $x_j(t)>0$, and wherein $A_j$ is an amplitude and $\omega$ is a stimulation frequency.

2. The device as claimed in claim 1, wherein the plurality of stimulation units comprise optical fibers configured to guide the optical stimuli to the plurality of respective stimulation location.

3. The device as claimed claim 1, wherein the optical stimuli are formed such that they do not trigger any action potentials in the stimulated neurons.

4. The device as claimed in claim 1, further comprising a measuring unit configured to record measurement signals measured on the patient.

5. The device as claimed in claim 4, wherein the control unit is configured to actuate the stimulation units depending on the recorded measurement signals.

6. The device as claimed in claim 4, wherein there is at least overlap between a period during which the stimulation units generate the optical stimuli and a period during which the measuring unit records measurement signals.

7. The device as claimed in claim 1, wherein the stimulation is performed for k successive periods, subsequently interrupted for m successive periods and resumed thereafter, where each of k and m is greater than or equal to 1.

8. The device as claimed in claim 1, wherein there is variation in the order in which the stimulation units generate the optical stimuli.

9. The device as claimed in claim 1, wherein the stimulation frequency $\omega$ is matched to a frequency of the abnormally synchronous and oscillatory neuronal activity of the neurons.

10. A method for resetting phases of neuronal activity, the method comprising:

implanting a plurality of stimulation units into the body of the patient at a plurality of respective stimulation locations; and controlling the stimulation units to generate optical stimuli to stimulate neurons at the plurality of respective stimulation locations, wherein the neurons exhibit an abnormally synchronous and oscillatory neuronal activity, wherein the optical stimuli are generated at the plurality of respective stimulation locations such that the phases of the neurons at the respective stimulation locations are reset at different times, wherein the number of stimulation units is N, wherein the j-th stimulation unit applies an optical stimulation signal $S_j(t)=A_j x_j(t)\theta[x_j(t)]$ to the respective stimulation location, with $j=1, 2, \ldots, N$ and $x_j(t)=\sin[\omega t+(j-1)2\pi/N]$ and $\theta[x_j(t)]=0$ for $x_j(t)\leq 0$ and $\theta[x_j(t)]=1$ for $x_j(t)>0$, and wherein $A_j$ is an amplitude and $\omega$ is a stimulation frequency.

11. The method as claimed in claim 10, wherein the stimulation frequency $\omega$ is matched to a frequency of the abnormally synchronous and oscillatory neuronal activity of the neurons.

\* \* \* \* \*